(12) United States Patent
Horwitz

(10) Patent No.: US 6,803,036 B1
(45) Date of Patent: Oct. 12, 2004

(54) USE OF CYTOKINES, CELLS AND MITOGENS TO INHIBIT GRAFT VERSUS HOST DISEASE

(75) Inventor: David A. Horwitz, Santa Monica, CA (US)

(73) Assignee: University of Southern California, Los Angeles, CA (US)

(*) Notice: Subject to any disclaimer, the term of this patent is extended or adjusted under 35 U.S.C. 154(b) by 245 days.

(21) Appl. No.: 09/653,924

(22) Filed: Sep. 1, 2000

Related U.S. Application Data

(63) Continuation of application No. 09/261,890, filed on Mar. 3, 1999, now Pat. No. 6,447,765.
(60) Provisional application No. 60/151,987, filed on Sep. 1, 1999, and provisional application No. 60/076,677, filed on Mar. 3, 1998.

(51) Int. Cl.$^7$ ...................... A61K 45/00; A61K 39/395; A01N 65/00; A01N 63/00
(52) U.S. Cl. ..................... 424/85.1; 424/85.2; 424/93.7; 424/93.71; 424/140.1; 424/154.1
(58) Field of Search ............................... 424/52.2, 93.7, 424/130.1, 577, 140.1, 154.1, 85.1, 93.71; 435/734

(56) References Cited

U.S. PATENT DOCUMENTS

| | | |
|---|---|---|
| 6,228,359 B1 | 5/2001 | Horwitz |
| 6,358,506 B1 | 3/2002 | Horwitz |
| 6,406,696 B1 * | 6/2002 | Bluestone |
| 6,447,765 B1 * | 9/2002 | Horwitz |

FOREIGN PATENT DOCUMENTS

| | | |
|---|---|---|
| WO | 93/17698 | 9/1993 |
| WO | 97/42324 | 11/1997 |
| WO | 99/25366 | 5/1999 |
| WO | 99/48524 | 9/1999 |
| WO | 00/66158 | 11/2000 |
| WO | WO 01/77299 A2 | 10/2001 |

OTHER PUBLICATIONS

Sykes M, Hoyles KA, Romick ML, Sachs DH. In vitro and in vivo analysis of bone marrow–derived CD3+, CD4–, CD8–, NK1.1+ cell lines. Cell Immunol. 129(2):478–93, 1990.*

Martin, "Overview of Marrow Transplantation Immunology", in Bone Marrow Transplantation (eds. Forman et al.) pp. 16–21, Boston, *Blackwell Scientific Publications* (1994).

Dupont, B., "Immunology of hematopoietic stem cell transplantation: a brief review of its history", *Immunol Reviews* 157:5–12 (1997).

Rodt, H., "Anti–lymphocytic antibodies and marrow transplantation. 3. Effect of heterologous anti–brain antibodies on acute secondary disease in mice", *Eur. J. Immunol* 4:25–29 (1974).

Vallera et al., "Bone marrow transplantation across major histocompatibility barriers in mice. Effect of elimination of T cells from donor grafts by treatment with monoclonal Thy–1.2 plus complement or antibody alone", *Transplantation* 31:218–222 (1981).

Martin et al., "Effects of in vitro depletion of T cells in HLA–identical allogeneic marrow grafts", *Blood* 66:664–672 (1985).

Patterson et al., "Graft rejection following HLA matched T–lymphocyte depleted bone marrow transplantation", *Br J Haematol* 63:221–230 (1986).

Goldman et al., "Bone marrow transplantation for chronic myelogenous leukemia in chronic phase. Increased risk for relapse associated with T–cell depletion", *Ann Intern Med* 108:806–814 (1988).

Lucas et al., "The development of cellular immunity to Epstein–Barr virus after allogeneic bone marrow transplantation", *Blood* 87:2594–2603 (1996).

Blazar et al., "FK506 inhibits graft–versus–host disease and bone marrow graft rejection in murine recipients of MHC disparate donor grafts by interfering with mature peripheral T cell expansion post–transplantation", *J. Immunol* 153:1836–1846 (1994).

Blazar et al., "Murine recipients of fully mismatched donor marrow are protected form lethal graft–versus–host disease by the in vivo administration of rapamycin but develop an autoimmune–like syndrome", *J. Immunol* 151:5726–5741 (1993).

Dumont et al., "Distinct Mechanisms of Suppression of Murine T Cell Activation by the Related macrolides FK–506 and Rapamycin", *J. Immunol* 144:251–258 (1990).

Morris, "Prevention and treatment of allograft rejection in vivo by rapamycin: molecular and celular mechanisms of action", *Ann NY Acad Sci* 685:68–72 (1993).

Gratama et al., "Treatment of Acute Graft–Versus–Host Disease With Monoclonal Antibody OKT3. Clinical results and effect on circulating T lymphocytes", *Transplantation* 38(5):469–474 (1984).

Hiruma et al., "Effects of anti–CD3 monoclonal antibody on engraftment of T–cell–depleted bone marrow allografts in mice: host T–cell suppression, growth factors, and space", *Blood* 79:3050–3058 (1992).

Anasetti et al., "Treatment of acute graft–versus–host disease with a nonmitogenic anti–CD3 monoclonal antibody", *Transplantation* 54:844–851 (1992).

(List continued on next page.)

*Primary Examiner*—Christina Chan
*Assistant Examiner*—Maher Haddad
(74) *Attorney, Agent, or Firm*—Richard F. Trecartin; Renee M. Kosslak; Dorsey & Whitney LLP

(57) ABSTRACT

The field of the invention is generally related to pharmaceutical agents useful in treating graft-versus-host disease (GVHD) in patients that have received allogenic bone marrow transplants.

18 Claims, 16 Drawing Sheets

OTHER PUBLICATIONS

Martin et al., "Effects of treating marrow with a CD3–specific immunotoxin for prevention of acute graft–versus–host disease", *Bone Marrow Transplant* 3:437–444 (1989).

Herve et al., "Treatment of Corticosteroid Resistant Acute Graft–Versus–Host Disease by In Vivo Administration of Anti–Interleukin–2 Receptor Monoclonal Antibody (B–B10)", *Blood* 75(4):1017–1023 (1990).

Boussiotis et al,. "B7 but not intercellular adhesion molecule–1 costimulation prevents the induction of human alloantigen–specif tolerance," *J Exp Med* 178:1753–1763 (1993).

Gribben et al., "Complete blockade of B7 family–mediated costimulation is necessary to induce human alloantigen–specific anergy: a method to ameliorate graft–versus–host disease and extend the donor pool", *Blood* 97:4887–4893 (1996).

Blazar et al., "Recent advances in graft–versus–host disease (GVHD)", *Immunol Rev* 157:79–90 (1997).

Krenger et al., "Effects of exogenous interleukin–10 in a murine model of graft–versus–host disease to minor histocompatibility antigens", *Transplantation* 58:1251–1257 (1994).

Pawelec, et al., "Cytokine Modulation of TH1/TH2 Phenotype Differentiation in Directly Alloresponsive CD4+ Human T Cells," *Transplantation* 62(8):1095–1101 (1996).

Halverson, et al., "In Vitro Generation of Allospecific Human CD8+ T Cells of Tc1 and Tc2 Phenotype," *Blood* 90(5):2089–2096 (1997).

Zeller, et al., "Ex vivo IL10 and TGF–Beta Act Synergistically to Induce CD4+ Alloantigen–Specific Tolerance Resulting in Diminished Graft–Versus–Host Disease in Vivo," *FASEB Journal* (Mar. 12, 1999) 12(4)part 1, A614. Meeting Info: Annual Meeting of the Professional Research Scientists for Experimental Biology. Apr. 17–21 1999.

Oswald, et al., "IL–10 Synergizes with IL–4 and Transforming Growth Factor–Beta to Inhibit macrophage Cytotoxic Activity," *J Immunology* 148(11):3578–3582 (1992).

Han, et al., "A New Type of CD4+ Suppressor T cell Completely Prevents Spontaneous Autoimmune Diabetes and Recurent Diabetes in Syngeneic Islet–Transplanted NOD Mice," *Journal of Autoimmunity*, 9:331–339 (1996).

Rook et al., "Effects of Transforming Growth Factor β on the Functions of Natural Killer Cells: Depressed Cytolytic Activity and Blunting of Interferon Responsiveness," *J Immunology* 136(10):3916–3920 (1986).

Gray et al., "Generation of an Inhibitory Circuit Involving CD8+ T Cells, IL–2 and NK Cell–Derived TGF–β: Contrasting Effects of Anti–CD2 and Anti–CD3", *J Immunol*, 160:2248–2254 (1998).

Gray et al., "The role of transforming growth factor beta in the generation of suppression: an interaction between CD8+ and NK cells", *J Exp Med* 180:1937–1942 (1994).

Blazar et al., Both CD4+ and CD8+ T Cells Can Cause Accelerated GVHD Lethality in the Presence of High In Vivo Doses of Exogenous Ill10: Role of Interfereon Gamma (IFNγ) in GVHD Induction, *Blood* 88:247 (1996) (abstract).

Krenger et al., "Polarized type 2 alloreactive CD4+ and CD8+ donor T cells fail to induce experimental acute graft–versus–host disease", *J Immunol* 153:585–593 (1995).

Fowler et al ., "Donor CD4–enriched cells of Th2 cytokine phenotype regulate graft–versus–host disease without impairing allogeneic engraftment in sublethally irradiated mice", *Blood* 84:3540–3549 (1994).

Bonini et al., HSY–TK gene transfer into donor lymphocytes for control of allogeneic graft–versus–leukemia, *Science* 276:1719–1724 (1997).

Storb et al., "Long–term follow–up of a controlled trial comparing a combination of methotrexate plus cyclosporine with cyclosporine alone for prophylaxis of graft–versus–host disease in patients administered HLA–identical marrow grafts for leukemia", *Blood* 80:560–561 (1992).

Sullivan et al., "Chronic Graft–Versus–Host Disease and Other Late Complications of Bone Marrow Transplantation", *Semin Hermatol* 28:250–259 (1992).

Via et al., "Critical Role of interleukin–2 in the development of acute graft–versus–host disease", *International Immunol* 5:565–572 (1993).

Fast, "Generation and characterization of IL–2–activated veto cells", *J Immunol* 149:1510–1515 (1992).

Hirohata et al., "Role of II–2 in the generation of CD4+ suppressors of human B cell responsiveness", *J Immunol* 142:3104–3112 (1989).

Taylor, "Antigen specific suppressor T cells respond to cytokines released by T cells", *Advances Exp Med Biol* 319:125–135 (1992).

Kinter et al., "Interleukin 2 induces CD8+ T cell–mediated suppression of human immunodeficiency virus replication in CD4+ T cells and this effect overrides its ability to sitmulate virus expression", *Proc. Natl. Acad. Sci. USA* 92: 10985–10989 (1995).

Barker et al., "Identification of multiple and distinct CD8+ T cell suppressor activities: dichotomy between infected and uninfected individuals, evolution with progression of disease, and sensitivity to gamma irradiation," *J Immunol* 156:4476–4483 (1996).

Hirokawa et al., "Human resting B lymphocytes can serve as accessory cells for anti–CD2–induced T cell activation", *J. Immunol.* 149:1859–1866, 1992.

Border et al., "Transforming growth factor–beta in disease: the dark side of tissue repair," *J Clin Invest* 90:1–7 (1992).

Sporn et al., "Some recent advances in the chemistry and biology of transforming growth factor–beta," *J Cell Biol* 105:1039–1045 (1987).

Massague, "Receptors for the TGF–bata family", *Cell* 69:1067–1070 (1992).

Murphy et al, "The potential role of NK cells in the separation of graft–versus–tumor effects from graft–versus–host disease after allogeneic bone marrow transplantation," *Immunol Rev* 157:167–176 (1997).

Chavin, et al., "Anti–CD2 mAbs Suppress Cytotoxic Lymphocyte Activity by the Generation of Th2 Suppressor Cells and Receptor Blockade," *J Immunol* 152:3729–3739 (1994).

Asano M, et al., "Autoimmune disease as a consequence of developmental abnormality of a T cell subpopulation." J Exp Med. Aug. 1, 1996;184(2):387–96.

Auchincloss, Hugh Jr., et al, in Fundamental Immunology 4th Ed., Paul, W.E. (ed.) Lippincot–Raven: Philadelphia New York; 1999 pp. 1182–1222.

Betz, M. and Fox, B.S., "Prostaglandin E2 inhibits production of Th1 lymphokines but not of Th2 lymphokines," J Immunol. Jan. 1, 1991;146(1):108–13.

Bonig H, et al., "Transforming growth factor–beta1 suppresses interleukin–15–mediated interferon–gamma production in human T lymphocytes." Scand J Immunol. Dec. 1999;50(6):612–8.

Bucy, R.P. et al., FASEB J. 1995 9:A497 (Abstract).

Chandrasekar, B., et al., "Dietary calorie restriction inhibits transforming growth factor–beta (TGF–beta) expressed in murine lupos nephritis", 9th International Congress on Immunology, 848 (1995).

Chong P. et al. "Inhibition of protein–kinase C in peripheral blood mononuclear cells of patients with systemic lupus erythematosus: effect on spontaneous immunoglobulin production," Autoimmunity, 10:227–231 (1991).

Cosimi, A.B., et al., "Treatment of acute renal allograft rejection with OKT3 monoclonal antibody," Transplantation. Dec. 1981;32(6):535–9.

Delgiudice, G., et al., "TGF–beta activity is increased in systemic lupus erythematosus (SLE) and progressive systemic sclerosis (PSS)", Arthritis and Rheumatism vol. 36 (9 Suppl.) p S196(Sep. 1993).

Dooms, H. et al., "IL–2 and IL–15 direct the outcome of inappropriate CD4+ T cell stimulation towards apoptosis and anergy respectively," European Cytokine Network, 9(3):169 (1998).

Fernandes, G., et al., "Calorie restriction delays autoimmune murine lupus by differentially modulating oncogenes and TGF– beta–1 expression", 9th International Congress on Immunlogy., 848 (1995).

Gao Q, et al., "CD4+CD25+ cells regulate CD8 cell anergy in neonatal tolerant mice." Transplantation. Dec. 27, 1999;68(12):1891–7.

Gray et al., "Activated Natural Killer Cells Can Induce Resting B Cells to Produce Immunoglobulin," Arthritis & Rheumatism, 37(9)suppl:S378 (1994).

Gray, J. D., et al., "Generation of an inhibitory Circuit Involving CD8+ T Cells, IL–2, and NK Cell–Derived TGF–$\beta$: Contrasting Effects of Anti–CD2 and Anti–CD3", Journal of Immunol., 160:2248–2254 (1998).

Groux, H., et al., "A CD4+ T–cell subset inhibits antigen–specific T–cell responses and prevents colitis," Nature. Oct. 16, 1997;389(6652):737–42.

Hahn, B.H., Dubois'Lupus Erythematosus, 5th Ed. (1997), pp. 69–76 (D.J. Wallace et al. eds., Williams and Wilkins, Baltimore).

Horwitz DA, et al., "Decreased production of interleukin–12 and other Th1–type cytokines in patients with recent–onset systemic lupus erythematosus." Arthritis Rheum. May 1998;41(5):838–44.

Horwitz, D.A., et al., "The immunoregulatory effects of NK cells: the role of TGF–$\beta$ and implications for autoimmunity", Immunology Today, vol. 18(11):538–542 (Nov. 1997).

Horwitz, D.A., Dubois'Lupus Erythematosus, 5th Ed. (1997), pp. 155–194 (D.J. Wallace et al. eds., Williams and Wilkins, Baltimore).

Huggins, M. L., et al., "Modulation of the Autoimmune Response in Lupus Mice by Oral Administration of Attenuated *Salmonella typhimurium* Expressing the IL–2 and TGF–$\beta$ Genes", Annals of New York Acad. of Sciences, vol. 815:499–502 (1997).

Jackson AL, et al., "Restricted expression of p55 interleukin 2 receptor (CD25) on normal T cells." Clin Immunol Immunopathol. Jan. 1990;54(1):126–33.

Jonuleit, H., et al., "Induction of interleukin 10–producing, nonproliferating CD4(+) T cells with regulatory properties by repetitive stimulation with allogeneic immature human dendritic cells," J Exp Med. Nov. 6, 2000:192(9):1213–22.

Kanegane H, et al., "A novel subpopulation of CD45RA+ CD4+ T cells expressing IL–2 receptor alpha–chain (CD25) and having a functionally transitional nature into memory cells." Int Immunol. Dec. 1991;3(12):1349–56.

Kirk, A.D., et al., "CTLA4–lg and anti–CD40 ligand prevent renal allograft rejection in primates," Proc Natl Acad Sci U S A. Aug. 5, 1997;94(16):8789–94.

Klinman DM, et al., "Quantitation of IgM– and IgG–secreting B cells in the peripheral blood of patients with systemic lupus erythematosus." Arthritis Rheum. Nov. 1991;34(11):1404–10.

Koide, J. and Engleman, E.G., "Differences in surface phenotype and mechanism of action between alloantigen specific CD8+ cytotoxic and suppressor T cell clones," J Immunol. Jan. 1, 1990;144(1):32–40.

Lancaster, R., et al., "Anti–idiotypic T cells suppress rejection of renal allografts in rats," Nature. May 23–29, 1985;315(6017):336–7.

Langrehr, J.M., et al., "Evidence that nitric oxide production by in vivo allosensitized cells inhibits the development of allospecific CTL," Transplantation. Mar. 1992;53(3):632–40.

Larsen, C.P., et al., "Long–term acceptance of skin and cardiac allografts after blocking CD40 and CD28 pathways," Nature. May 30, 1996;381(6581):434–8.

Linker–Israeli M, et al., "CD8+ lymphocytes from patients with systemic lupus erythematosus sustain, rather than suppress, spontaneous polyclonal IgG production and synergize with CD4+ cells to support autoantibody synthesis." Arthritis Rheum. Aug. 1990;33(8):1216–25.

Massague J., "The transforming growth factor–beta family." Annu Rev Cell Biol. 1990;6:597–641.

Mizuochi, T., et al., "Both L3T4+ and Lyt–2+ helper T cells initiate cytotoxic T lymphocyte responses against allogenic major histocompatibility antigens but not against trinitrophenyl–modified self," J Exp Med. Aug. 1 1985;162(2):427–43.

Mysliwietz J and Thierfelder S., "Antilymphocytic antibodies and marrow transplantation. XII. Suppression of graft–versus–host disease by T–cell–modulating and depleting antimouse CD3 antibody is most effective when preinjected in the marrow recipient." Blood. Nov. 15, 1992;80(10):2662–7 (Abstract).

Ohtsuka, K., et al., "Decreased Production of TGF–$\beta$ by Lymphocytes from Patients with Systemic Lupus Erythematosus", J. Immunol. 160:2539–2545 (1998).

Papiernik M, et al., "T cell deletion induced by chronic infection with mouse mammary tumor virus spares a CD25–positive, IL–10–producing T cell population with infectious capacity." J Immunol. May 15, 1997;158(10):4642–53.

Pearce, N.W., et al., "Specific unresponsiveness in rats with prolonged cardiac allograft survival after treatment with cyclosporine. V. Dependence of CD4+ suppressor cells on the presence of alloantigen and cytokines, including interleukin 2," Transplantation. Feb. 1993;55(2):374–80.

Pescovitz, M.D., et al., "Effect of class II antigen matching on renal allograft survival in miniature swine," J Exp Med. Nov. 1, 1984;160(5):1495–508.QIN, L., et al., "Gene transfer for transplantation. Prolongation of allograft survival with transforming growth factor–beta 1," Ann Surg. Oct. 1994;220(4):508–18; discussion 518–9.

Powrie, F., et al., "A critical role for transforming growth factor–beta but not interleukin 4 in the suppression of T helper type 1–mediated colitis by CD45RB(low) CD4+ T cells." J Exp Med. Jun. 1, 1996;183(6):2669–74.

Qin, L., et al., "Gene transfer for transplantation. Prolongation of allograft survival with transforming growth factor–beta 1," Ann Surg. Oct. 1994;220(4):508–18; discussion 518–9.

Qin, L. et al., "Retrovirus–mediated transfer of viral IL–10 gene prolongs murine cardiac allograft survival," J Immunol. Mar. 15, 1996;156(6):2316–23.

Raju, G.P., et al., "Prolongation of cardiac allograft survival with transforming growth factor–beta 1 in rats," Transplantation. Aug. 15, 1994;58(3):392–6.

Ramsdell, F. and Fowlkes, B.J., "Maintenance of in vivo tolerance by persistence of antien," Science. Aug. 21, 1992;257(5073):1130–4.

Read S, et al., "Cytotoxic T lymphocyte–associated antigen 4 plays an essential role in the function of CD25(+)CD4(+) regulatory cells that control intestinal inflammation." J Exp Med. Jul. 17, 2000;192(2):295–302.

Rocha, B., et al., "Clonal anergy blocks in vivo growth of mature T cells and can be reversed in the absence of antigen," J Exp Med. May 1, 1993;177(5):1517–21.

Roser, B.J., "Cellular mechanisms in neonatal and adult tolerance," Immunol Rev. Feb. 1989;107:179–202.

Sakaguchi S. et al., "Organ–specific autoimmune diseases induced in mice by elimination of T cell subset. I. Evidence for the active participation of T cells in natural self–tolerance; deficit of a T cell subset as a possible cause of autoimmune disease." J Exp Med. Jan. 1, 1985;161(1):72–87.

Sakaguchi, S., et al., "Immunologic self–tolerance maintained by activated T cells expressing IL–2 receptor alpha–chains (CD25). Breakdown of a single mechanisms of self–tolerance causes various autoimmune diseases," J Immunol Aug. 1, 1995;155(3):1151–64.

Seddon, B. and Mason, D., "The third function of the thymus," Immunol Today. Feb. 2000;21(2):95–9.

Shevach, E.M., "Regulatory T cells in autoimmunity," Annu Rev Immunol. 2000; 18:423–49.

Shivakumar S, et al., "T cell receptor alpha/beta expressing double–negative (CD4–/CD8–) and CD4+ T helper cells in humans augment the production of pathogenic anti–DNA autoantibodies associated with lupus nephritis." J Immunol. Jul. 1, 1989;143(1):103–12.

Singer, A., et al., "Self recognition in allogeneic radiation bone marrow chimeras. A radiation–resistant host element dictates the self specificity and immune response gene phenotype of T–helper cells," J Exp Med. May 1, 1981;153(5):1286–301.

Snijdewint, F.G., et al., "Prostaglandin E2 differentially modulates cytokine secretion profiles of human T helper lymphocytes," J Immunol. Jun. 15, 1993;150(12):5321–9.

Starzl, T.E., et al., "Chimerism and donor–specific nonreactivity 27 to 29 years after kidney allotransplantation," Transplantation. Jun. 1993;55(6):1272–7.

Strand, V., "Approaches to the management of systemic lupus erythematosus," Current Opinion in Rheumatology, 9:410–420 (1997).

Suri–Payer E, et al., "CD4+CD25+ T cells inhibit both the induction and effector function of autoreactive T cells and represent a unique lineage of immunoregulatory cells." J Immunol. Feb. 1, 1998;160(3):1212–8.

Suri–Payer E, et al., "Post–thymectomy autoimmune gastritis: fine specificity and pathogenicity of anti–H/K ATPase–reactive T cells." Eur J Immunol. Feb. 1999;29(2):669–77.

Taams, L.S., et al., "Anergic T cells actively suppress T cell responses via the antigen–presenting cell," Eur J Immunol. Sep. 1998;28(9):2902–12.

Takahashi T, et al., "Human CD8+ lymphocytes stimulated in the absence of CD4+ cells enhance IgG production by antibody–secreting B cells." Clin Immunol Immunopathol Mar. 1991;58(3):352–65.

Takahashi T, et al., "Immunologic self–tolerance maintained by CD25+CD4+ naturally anergic and suppressive T cells: induction of autoimmune disease by breaking their anergic/suppressive state." Int. Immunol. Dec. 1998;10(12):1969–90.

Thornton AM and Shevach EM. "CD4+CD25+ immunoregulatory T cells suppress polyclonal T cell activation in vitro by inhibiting interleukin 2 production." J Exp Med. Jul. 20, 1998;188(2):287–96.

Thornton AM and Shevach EM. "Suppressor effector function of CD4+CD25+ immunoregulatory T cells is antigen nonspecific." J Immunol. Jan. 1, 2000;164(1):183–90.

Tomita, Y., et al., "Importance of suppressor T cells in cyclophosphamide–induced tolerance to the non–H–2–encoded alloantigens. Is mixed chimerism really required in maintaining a skin allograft tolerance?" J Immunol. Jan. 15, 1990;144(2):463–73.

Vendetti, S., et al., "Anergic T cells inhibit the antigen–presenting function of dendritic cells," J Immunol. Aug. 1, 2000;165(3):1175–81.

Verbanac, K.M., et al., A role for transforming growth factor–beta in the veto mechanism in transplant tolerance Transplantation. Mar. 27, 1994;57(6):893–900.

Wahl SM. "Transforming growth factor beta: the good, the bad, and the ugly." J Exp Med. Nov. 1, 1994;180(5):1587–90.

Wekerle, T., et al., "Anti–CD154 or CTLA4Ig obviates the need for thymic irradiation in a non–myeloablative conditioning regimen for the induction of mixed hematopoietic chimerism and tolerance," Transplantation. Nov. 15, 1999;68(9):1348–55.

Weiner HL, et al., "Oral tolerance: immunlogic mechanisms and treatment of animal and human organ–specific autoimmune diseases by oral administration of autoantigens." Annu Rev. Immunol. 1994;12:809–37.

Wilson, D.B., "Idiotypic regulation of T cells in graft–versus–host disease and autoimmunity," Immunol Rev. Feb. 1989;107:159–77.

Zheng, X.X., et al., "Administration of noncytolytic IL–10/Fc in murine models of lipopolysaccharide–induced septic shock and allogeneic islet transplantation," J Immunol. May 15, 1995;154(10):5590–600.

Martin, P.J. et al., "Treatment of Acute Graft–Versus–Host Disease with Anti–CD3 Monoclonal Antibodies," Am Jour Kidney Disease 11(2):149–152 (1988).

Heitger A, et al. "Essential role of the thymus to reconstitute naive (CD45RA+) T–helper cells after human allogeneic bone marrow transplantation." Blood. Jul. 15, 1997;90(20):850–7.

Chen W, et al., "T cells specific for a polmorphic segment of CD45 induce graft–versus–host disease with predominant pulmonary vasculitis." J Immunol. Jul. 15, 1998;161(2):909–18.

Early E, and Reen DJ. "Rapid conversion of naive to effector T cell function counteracts diminished primary human newborn T cell responses." Clin Exp Immunol. Jun. 1999;16(3):527–33. (Abstract).

Garderet L, et al., "Effective depletion of alloreactive lymphocytes from peripheral blood mononuclear cell preparations." Transplantation. Jan. 15, 1999;67(1):124–30.

Asai O, et al., "Suppression of graft–versus–host disease and amplification of graft–versus–tumor effects by activated natural killer cells after allogeneic bone marrow transplantation," *Journal of Clinical Investigation* 101(9):1835–1842 (1998).

Zehavi–Willner et al., "The Mitogenic Acitvity of Staphylococcal Enterotixin B (SEB): A Monovalent T Cell Mitogen That Stimulates Cytoloytic T Lymphocytes but Cannot Mediate Their Lytic Interaction," *Journal of Immunology* 127(8):2682–2687 (1986).

Koh et al., "Adoptive cellular immunotherapy: NK cells and bone marrow transplantation," *Histol Histopathol* *15:1201–1210* (*2000*).

Zeller et al., Induction of CD4+T Cell Alloantigen–Specific Hyporesponsiveness by IL–10 and TGF–$\beta^1$, *Journal of Immunology* 163:3684–3691 (1999).

Boussiotis, "Altered T–cell receptor + CD28–mediated singnaling and blocked cell cycle progression in interleukin 10 and transforming growth factor–$\beta$–treated alloreactive T cells that do not induce graft–versus–host disease," *Blood* 97:5665–571 (2001).

\* cited by examiner

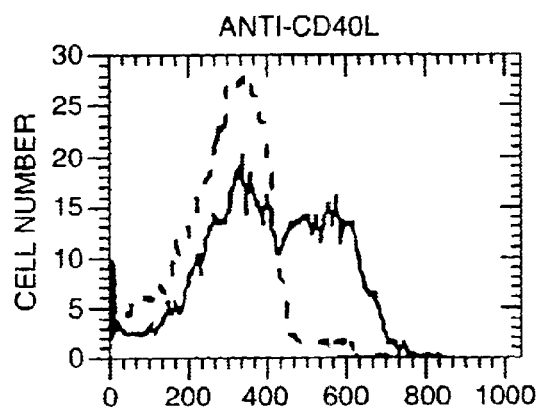
FIG._1A
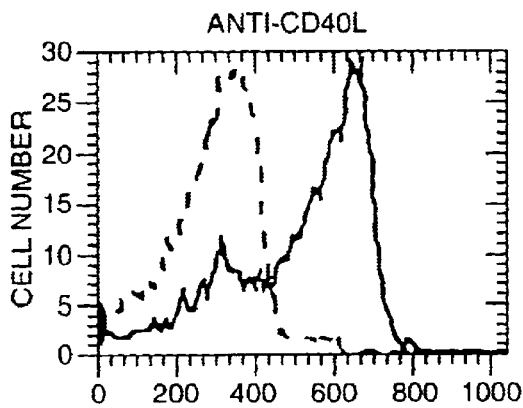
FIG._1B
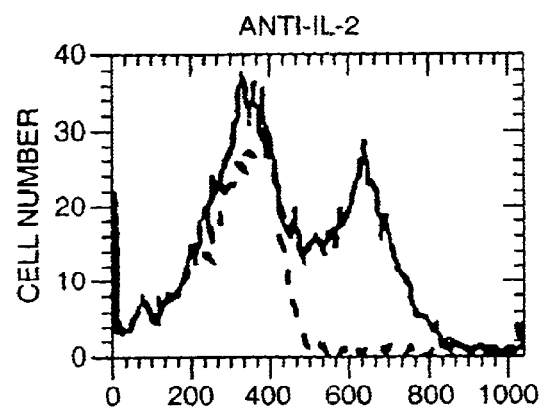
FIG._3A
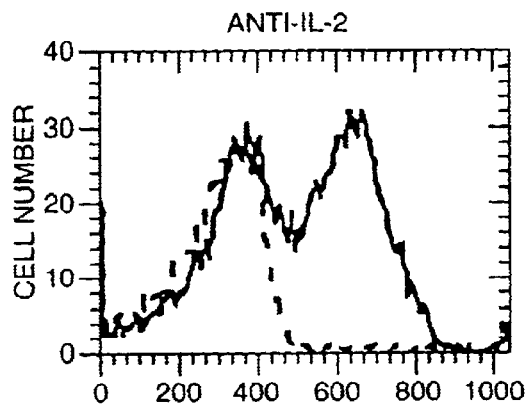
FIG._3B

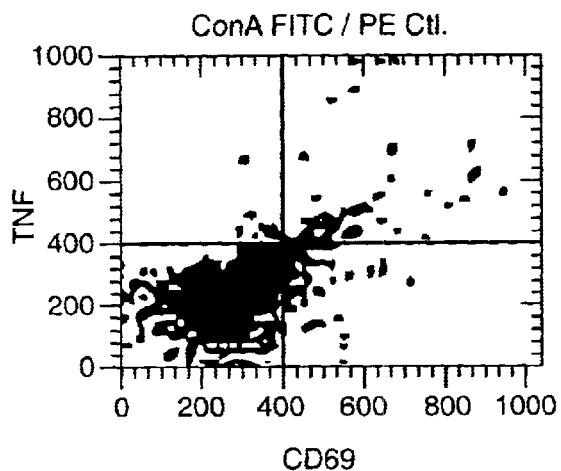
FIG._2A
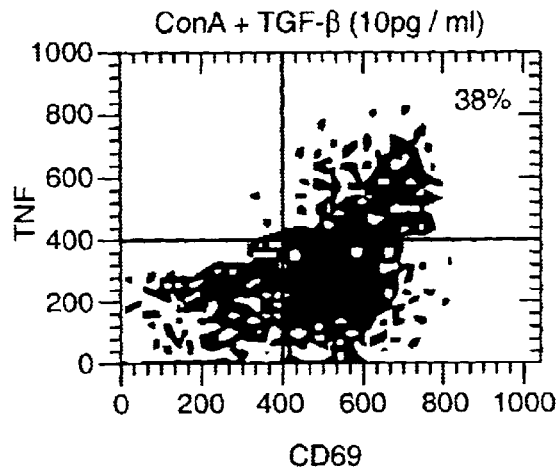
FIG._2B
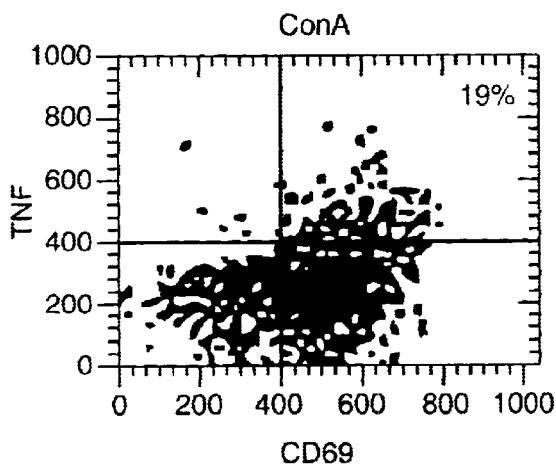
FIG._2C
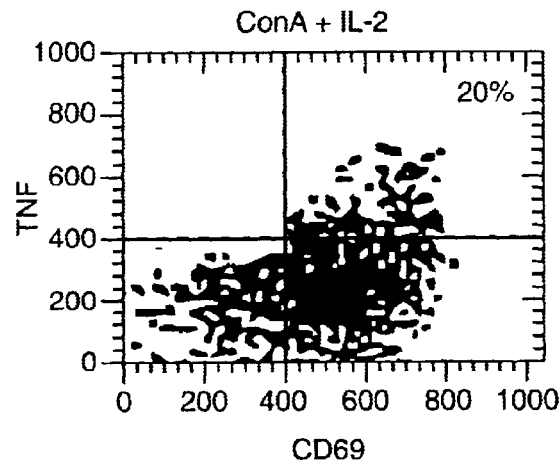
FIG._2D

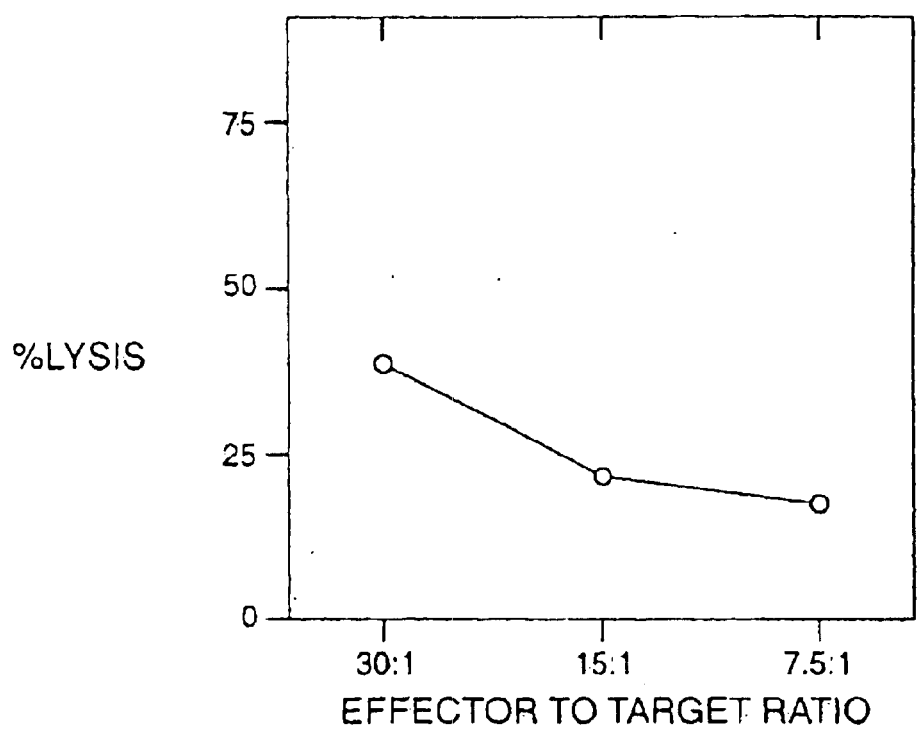
FIG._4A
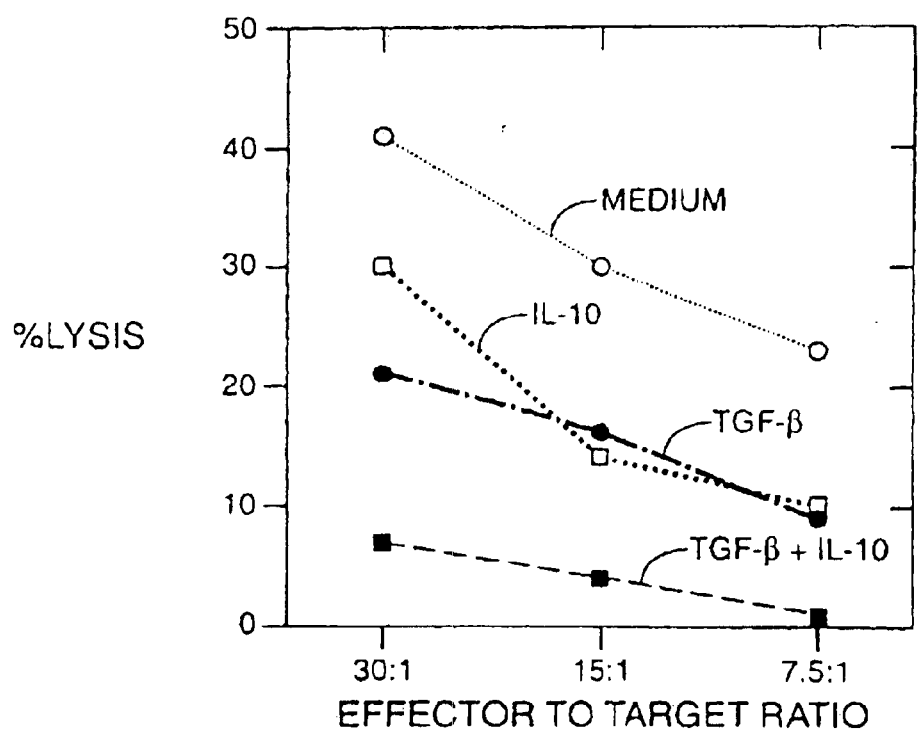
FIG._4B

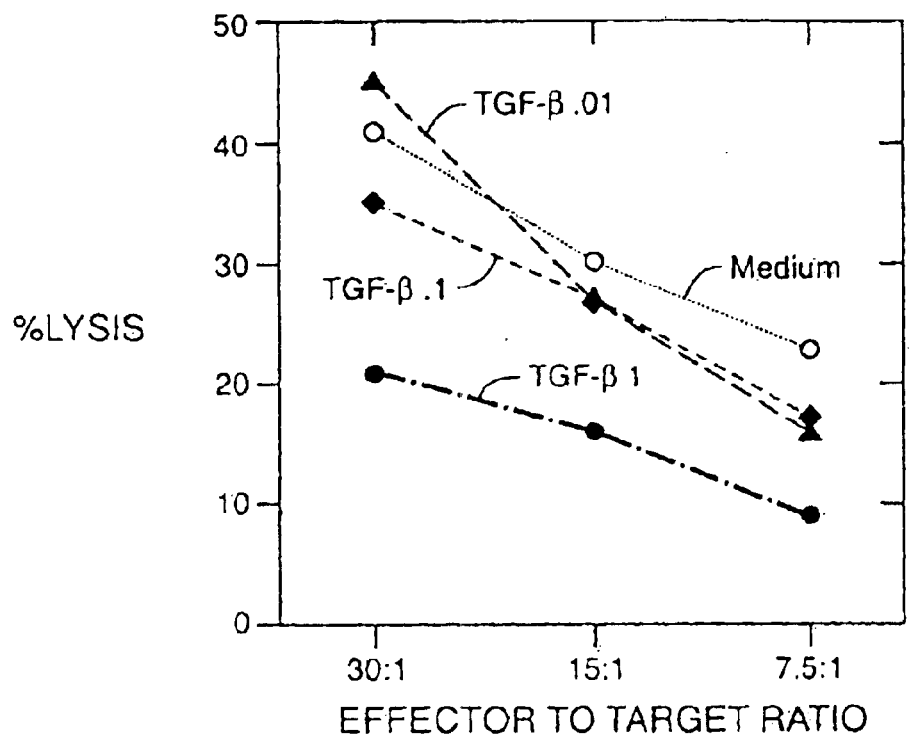
FIG._4C
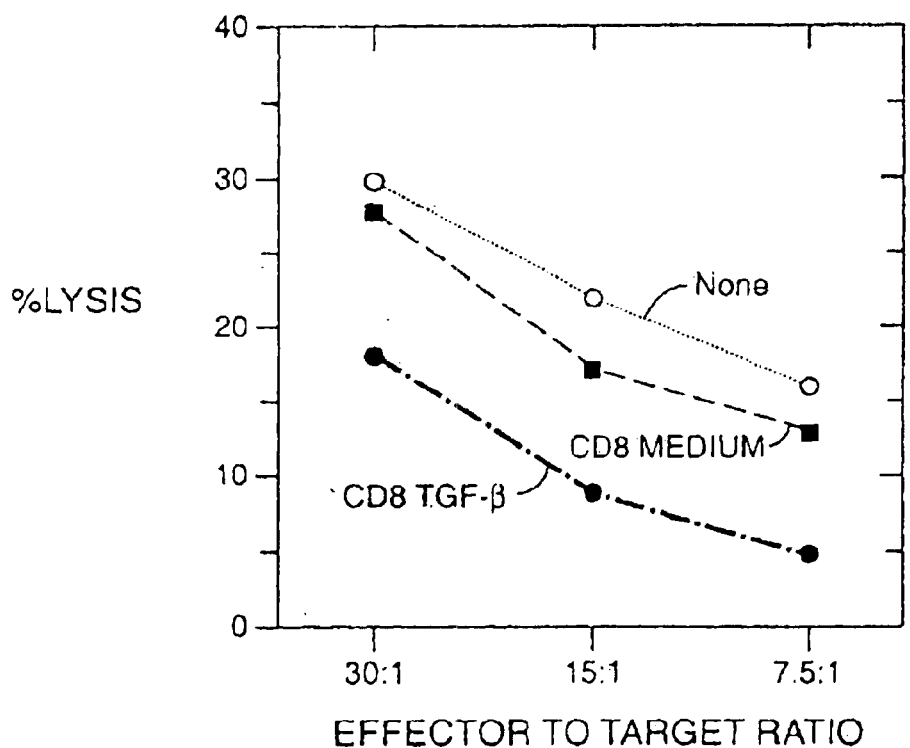
FIG._5

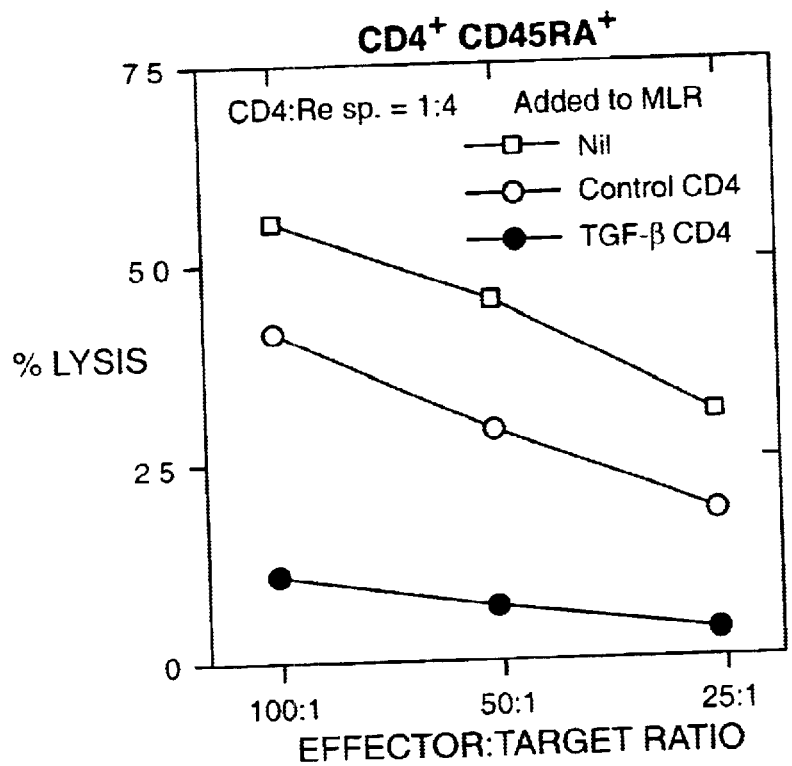
FIG._6A
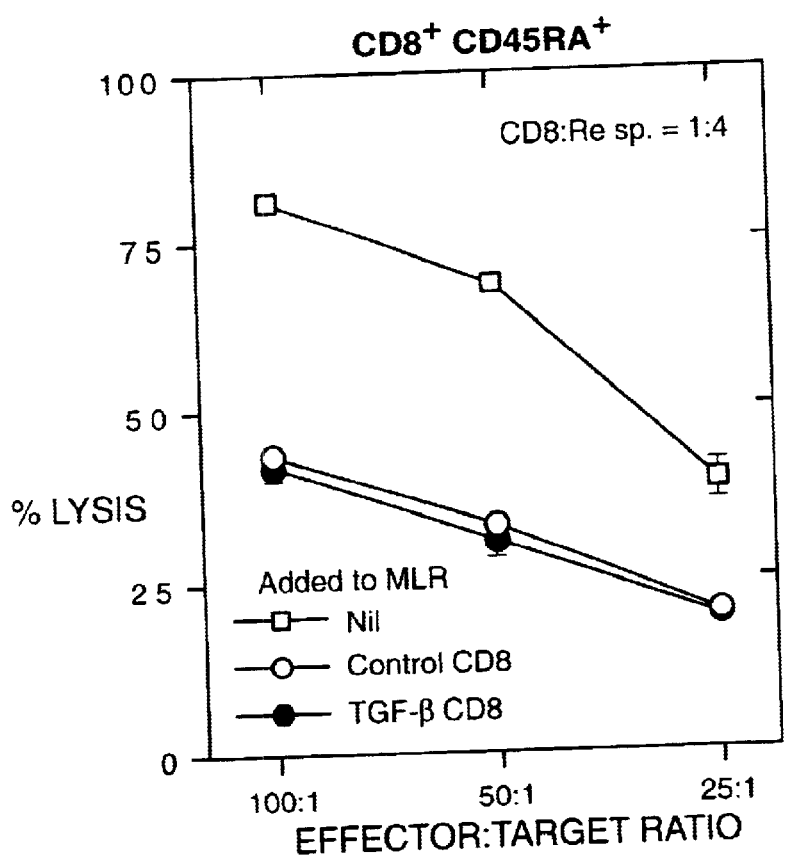
FIG._6B

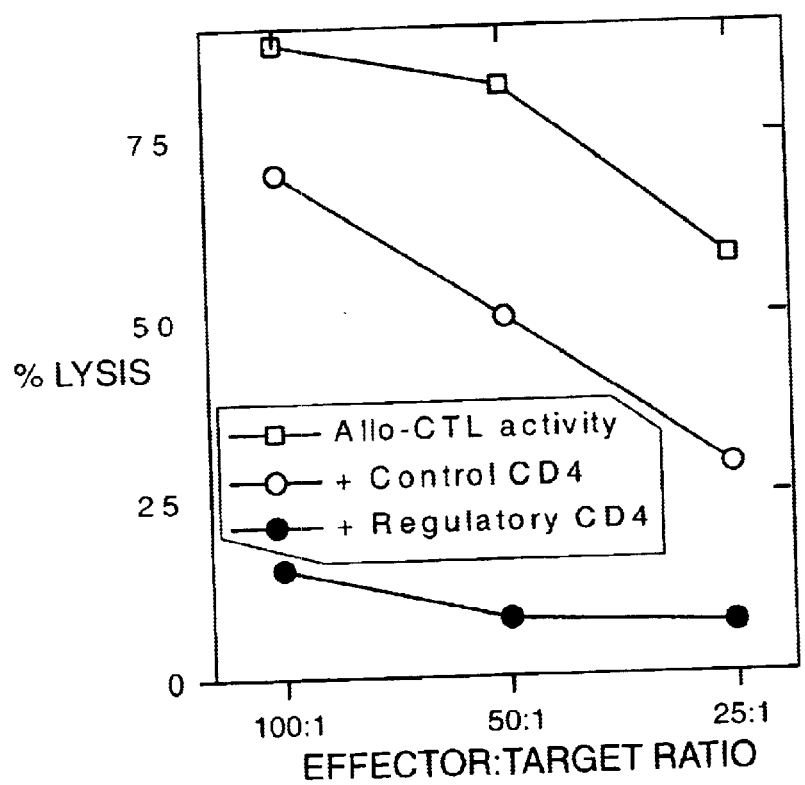
FIG._7A
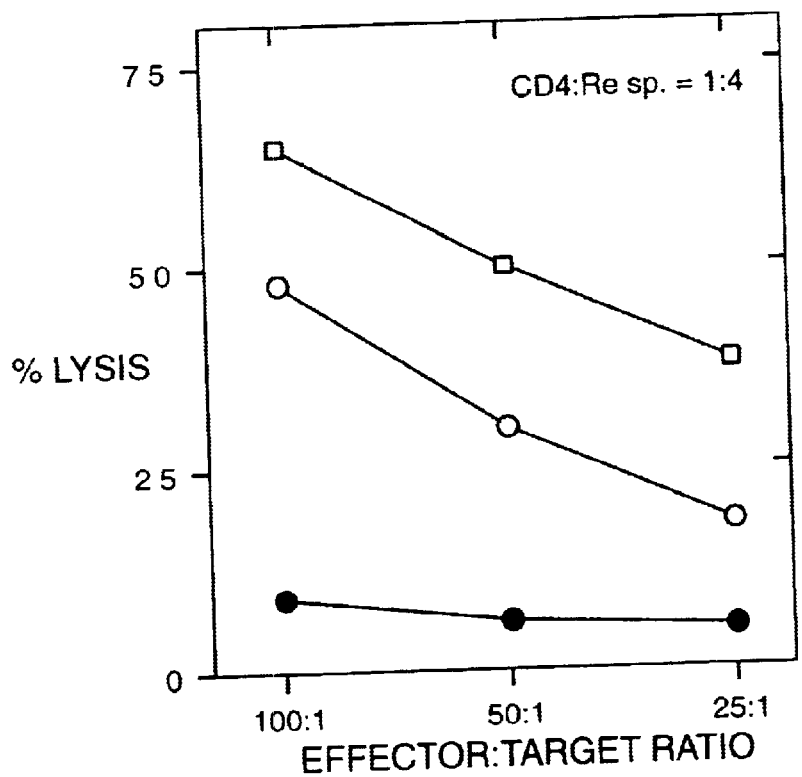
FIG._7B

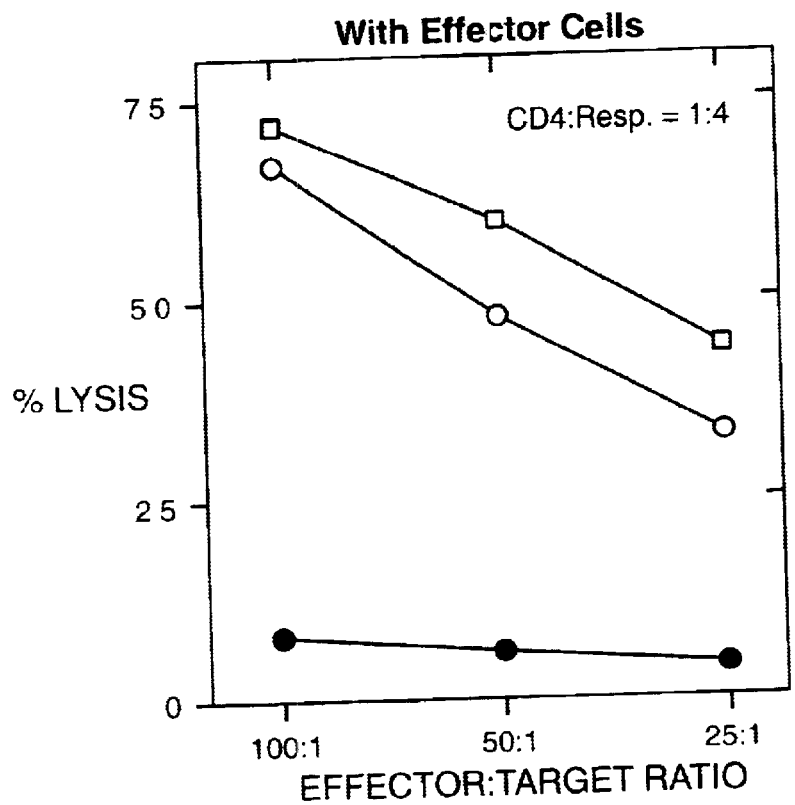
FIG._8A
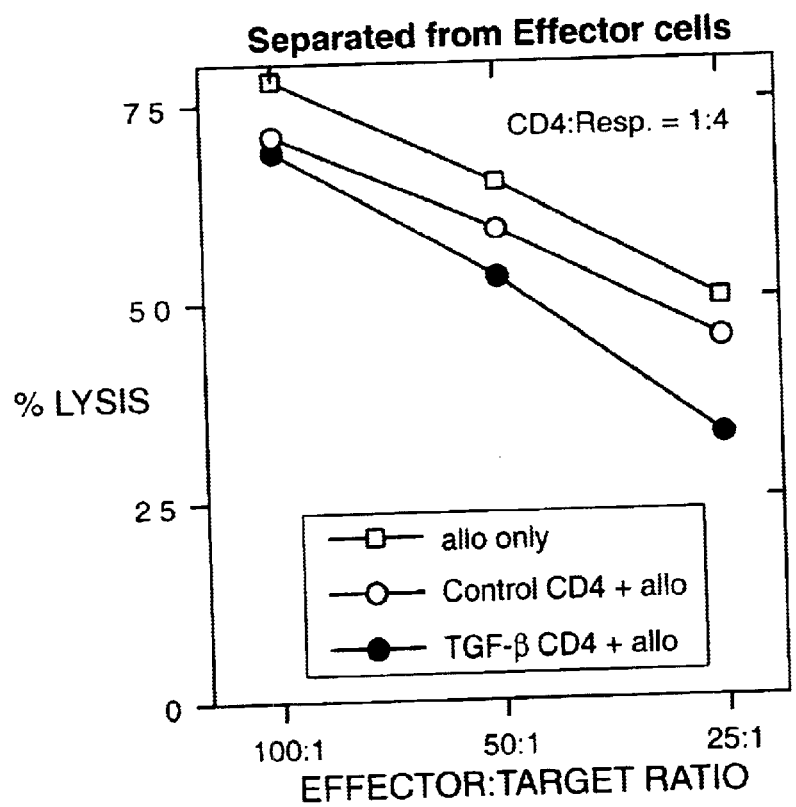
FIG._8B

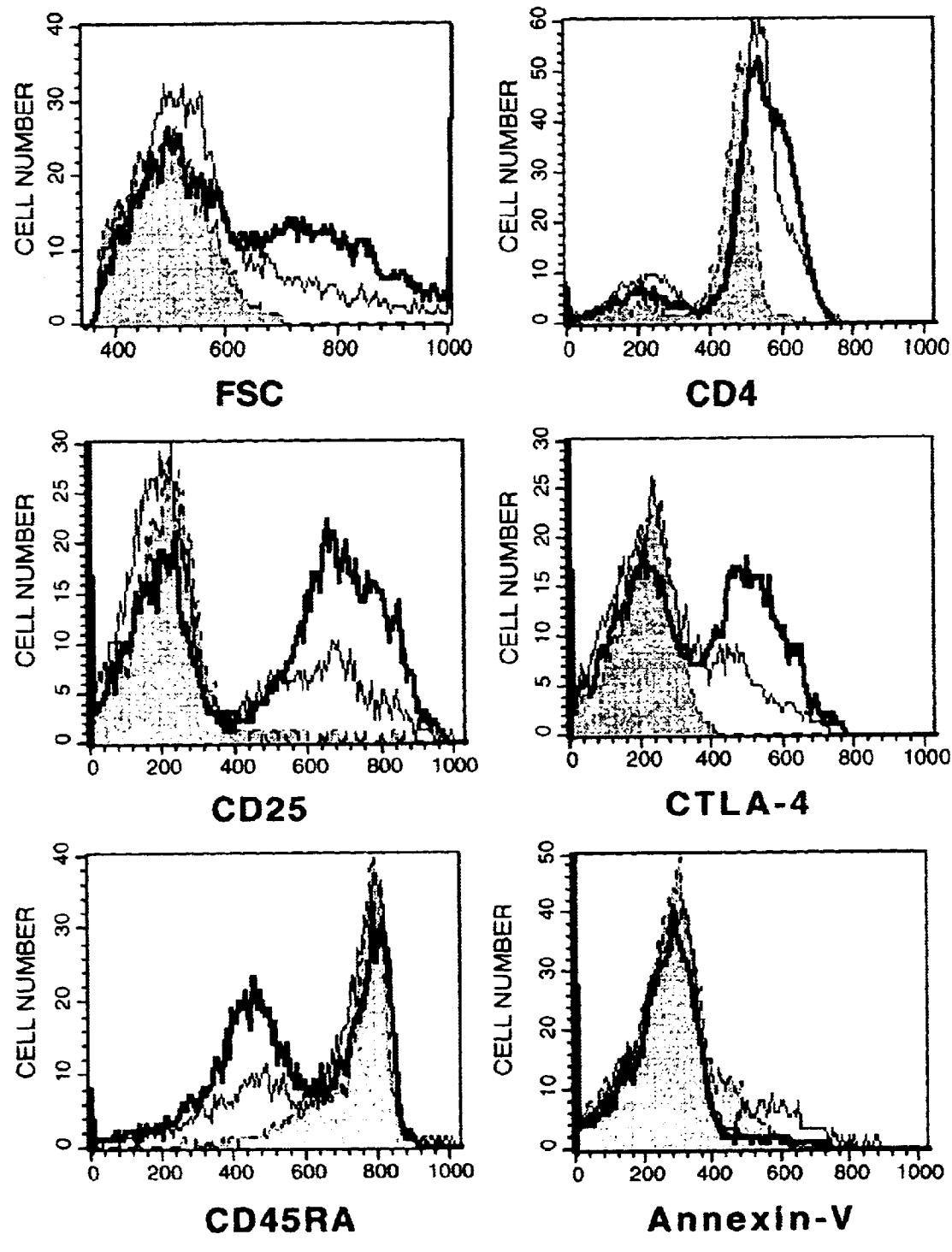
FIG._9

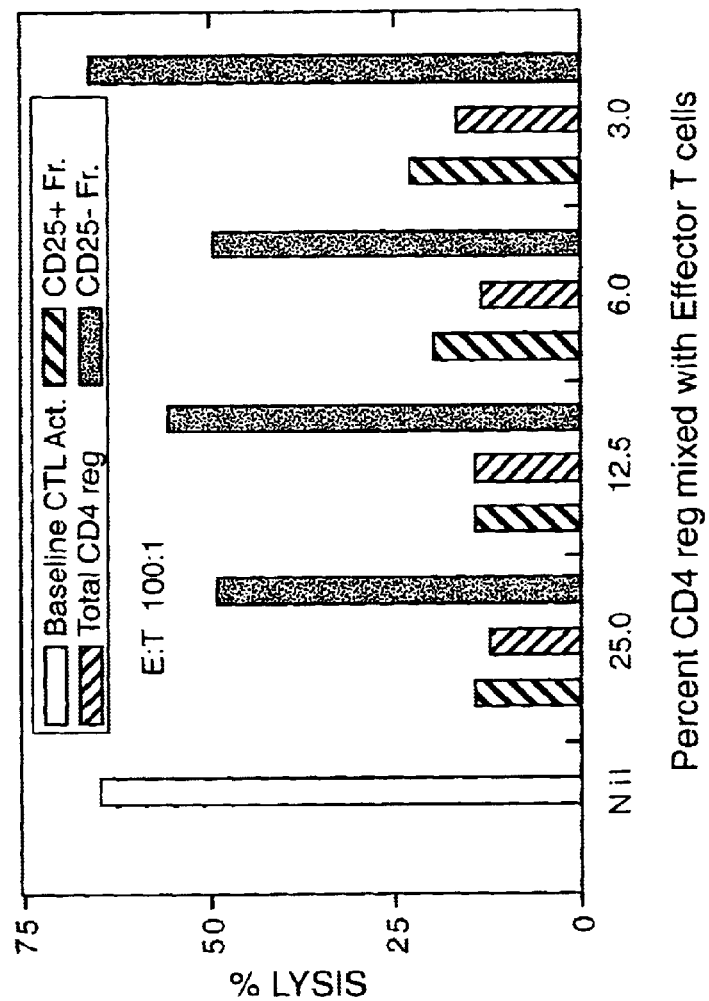
FIG. _ 10B
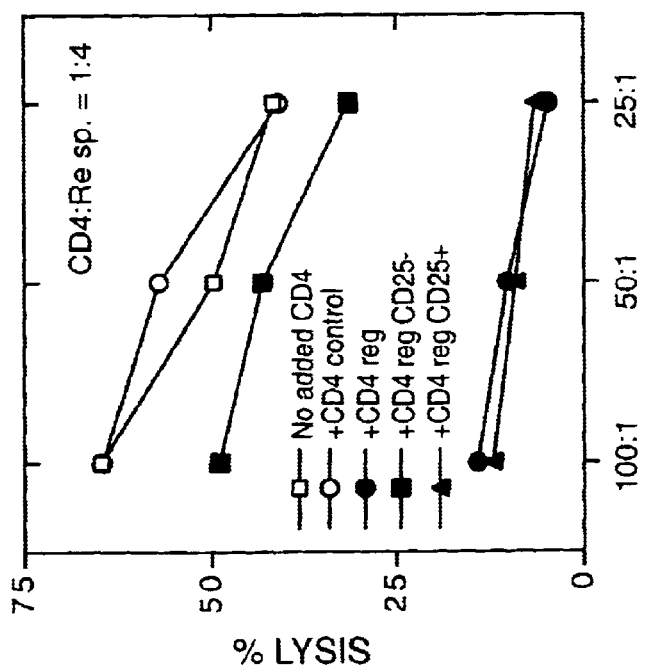
FIG. _ 10A

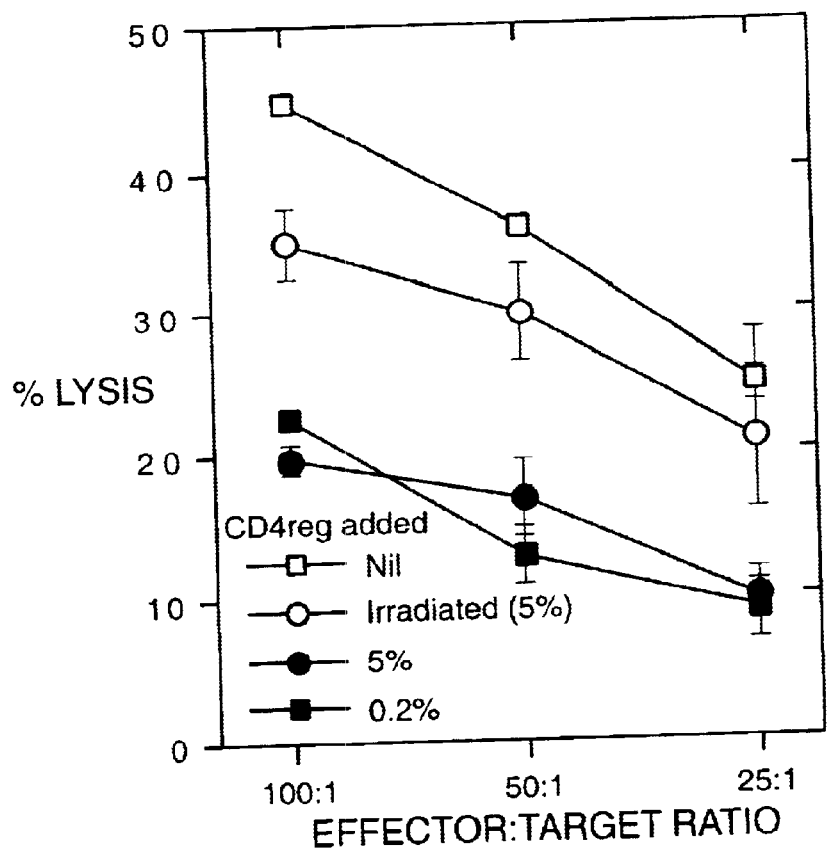
FIG._11
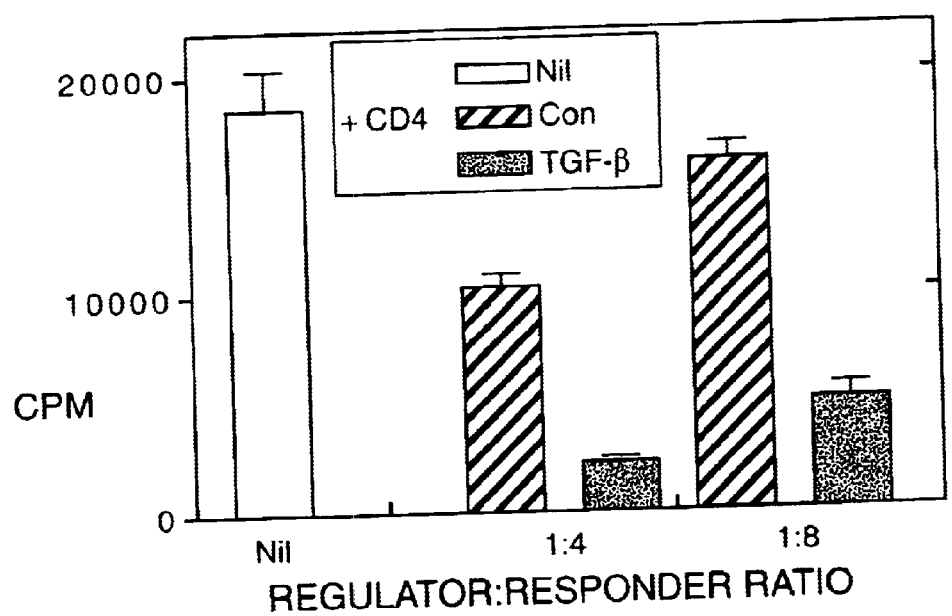
FIG._12

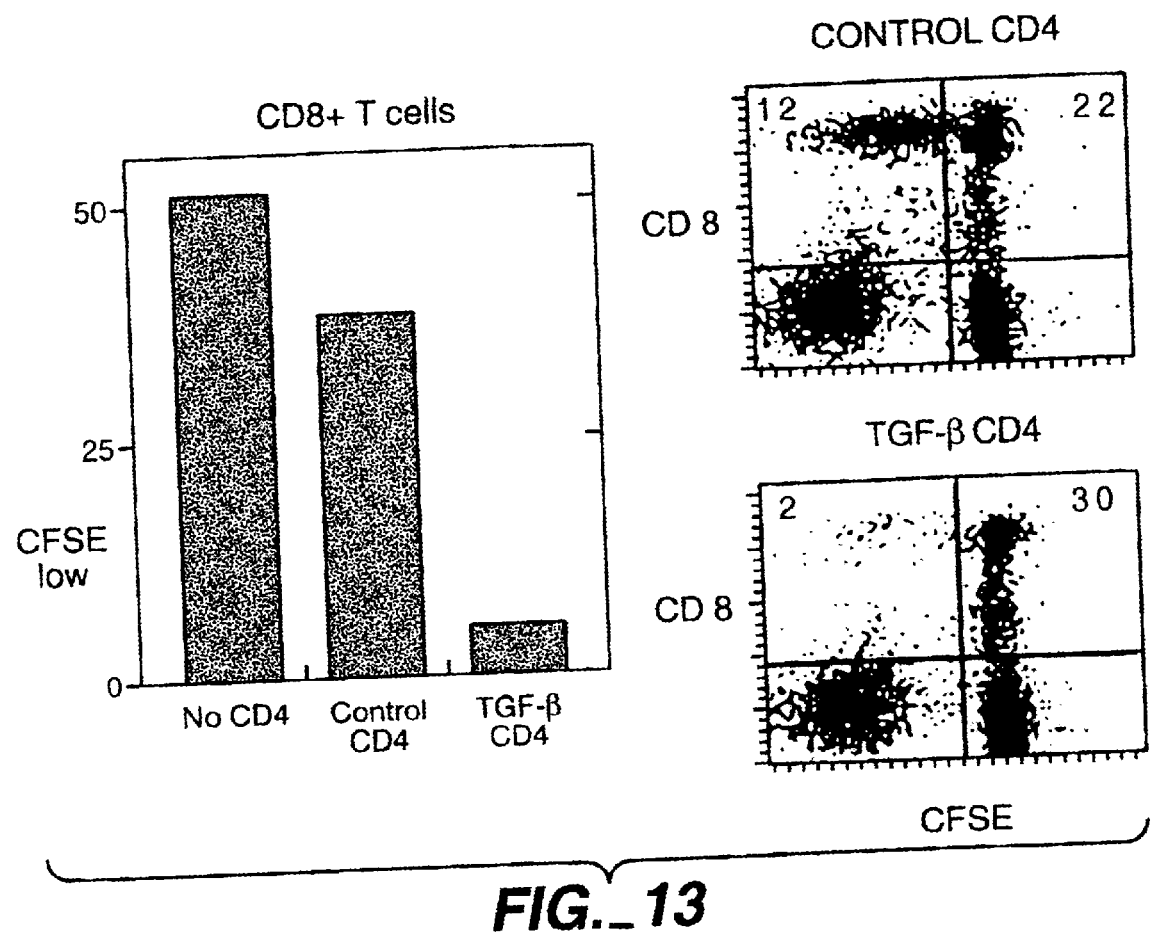
FIG._13
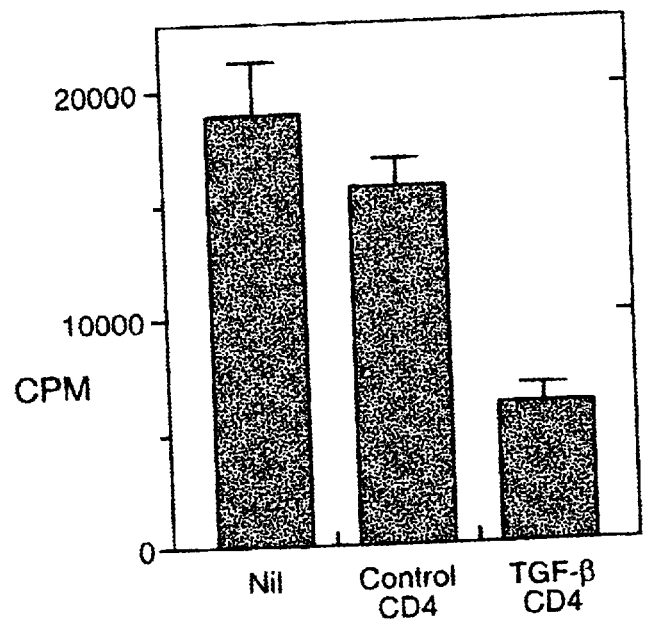
FIG._14A

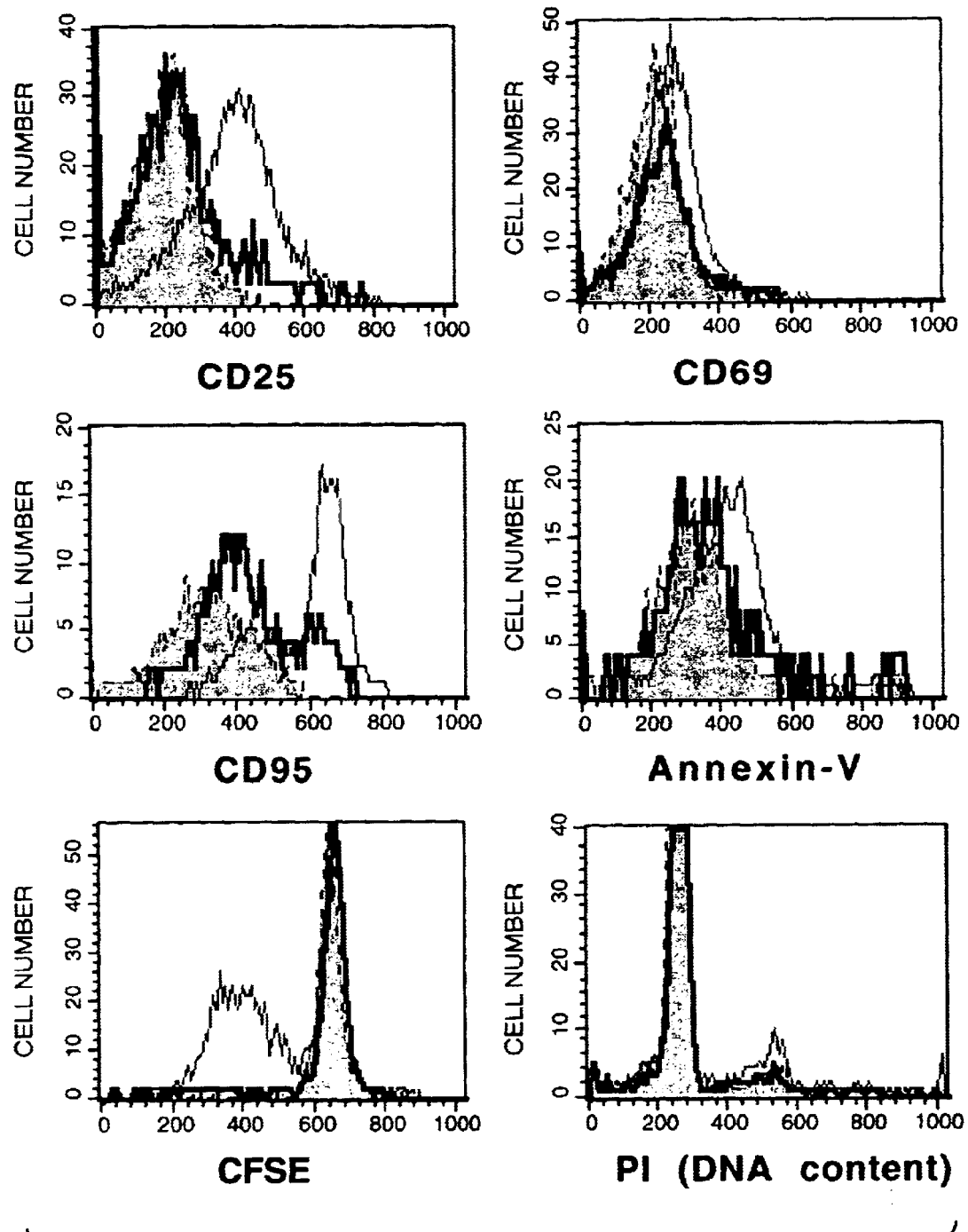
FIG._14B

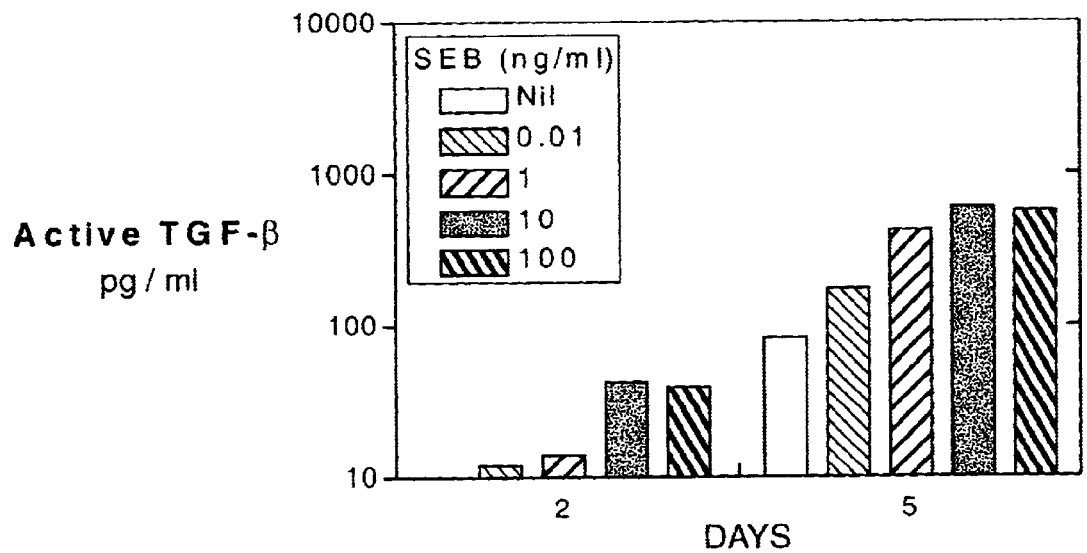
FIG._15A
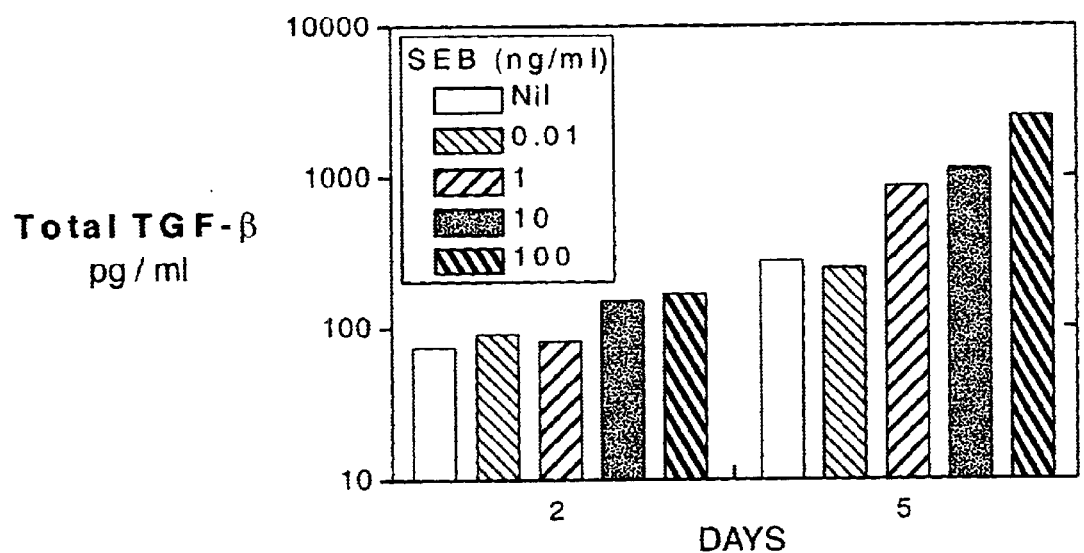
FIG._15B

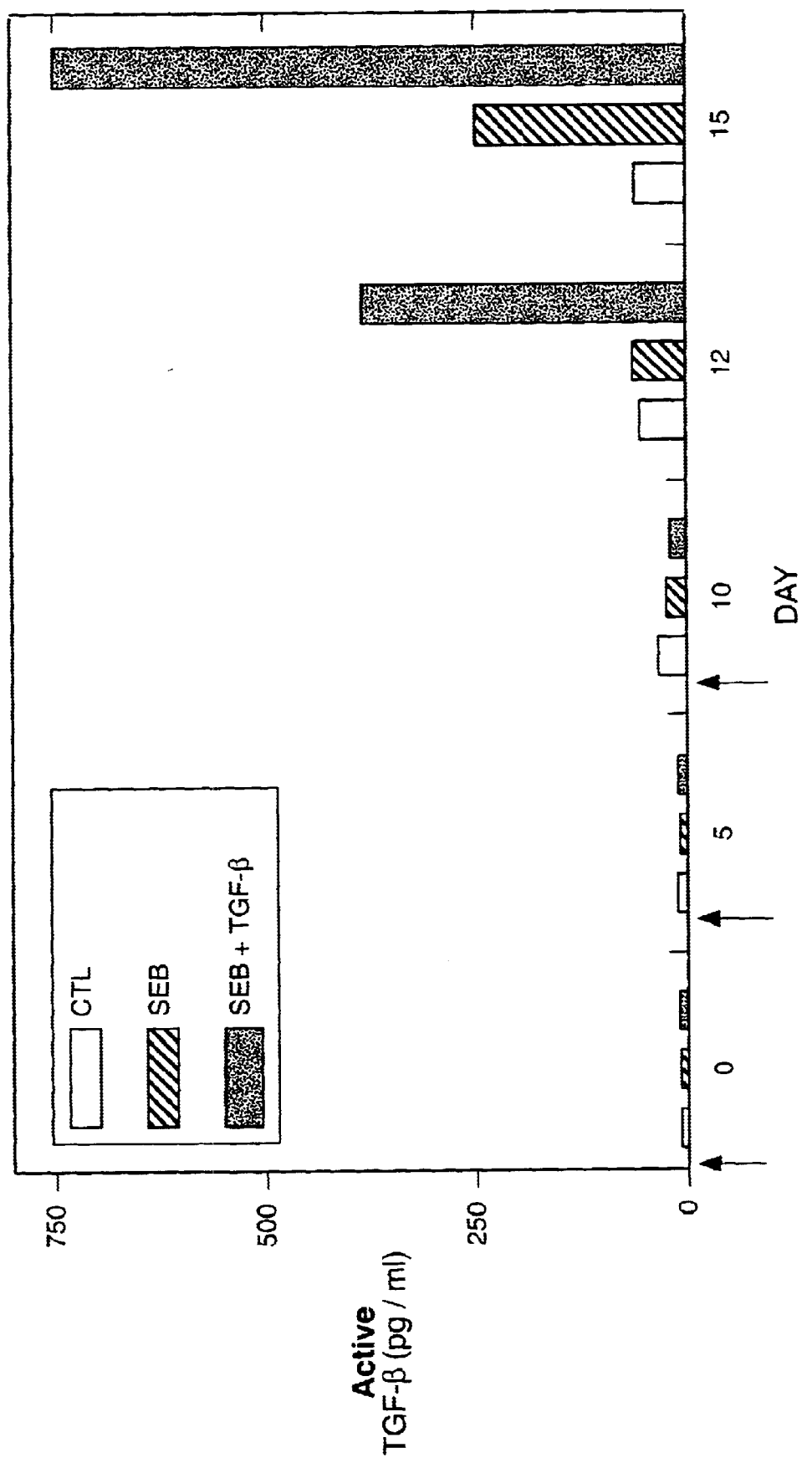
FIG._16

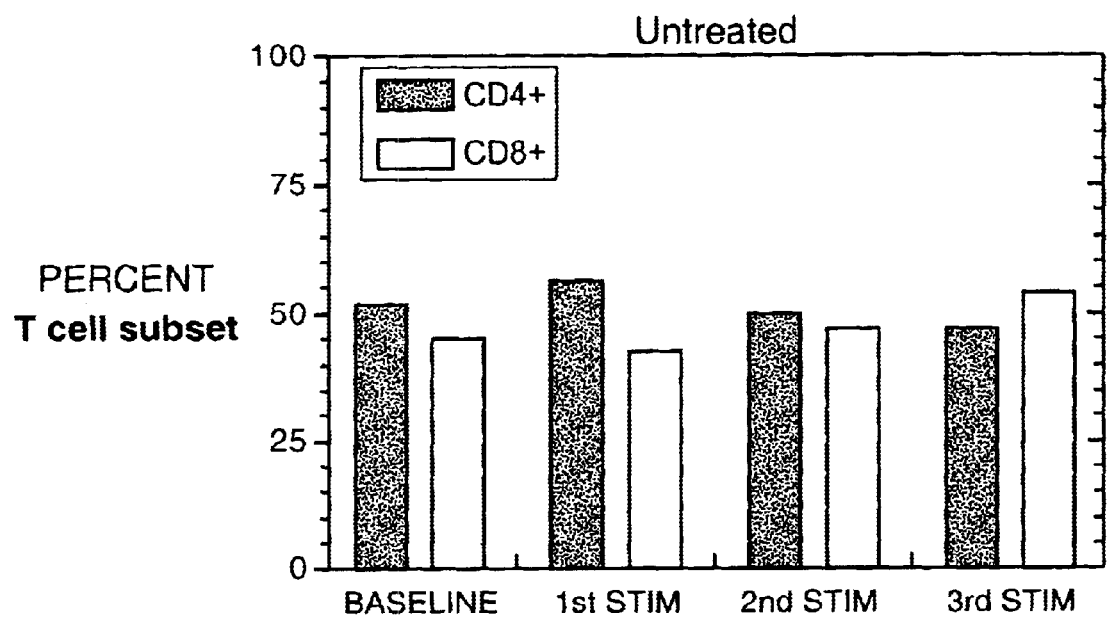
FIG._17A
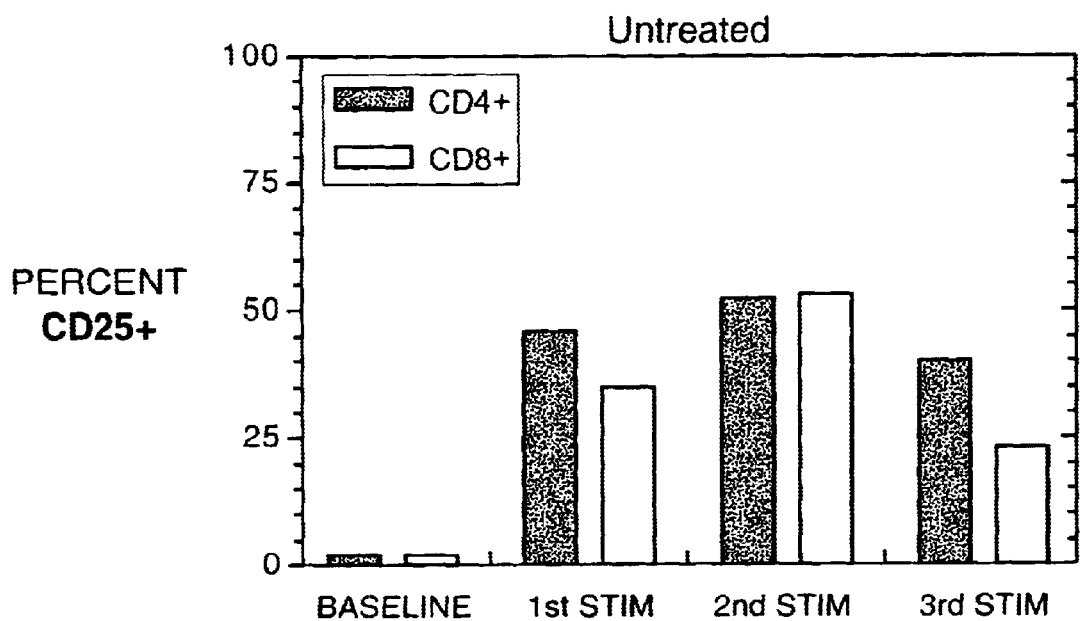
FIG._17B

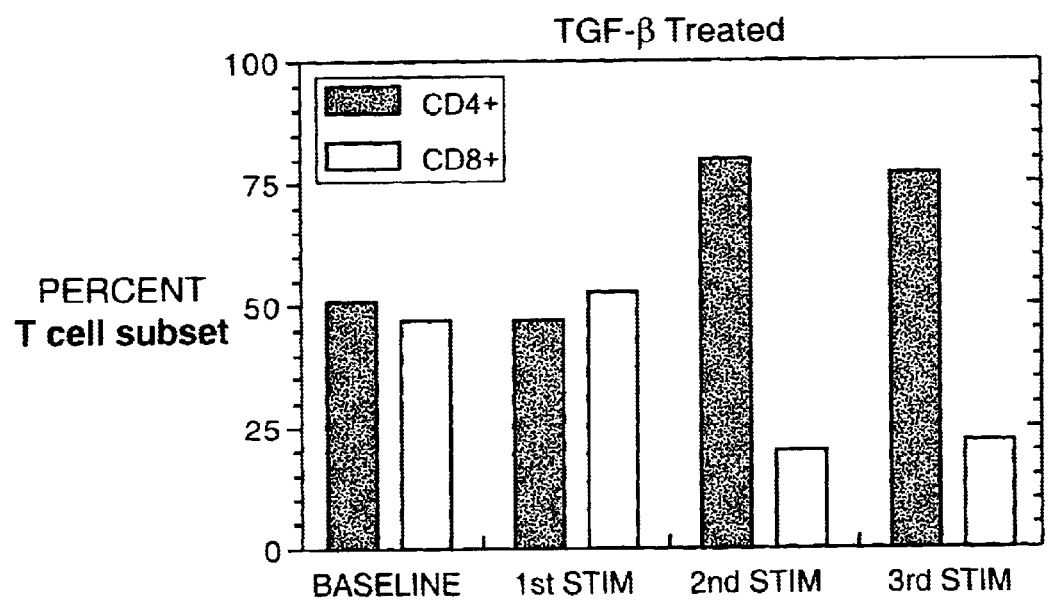
FIG._17C
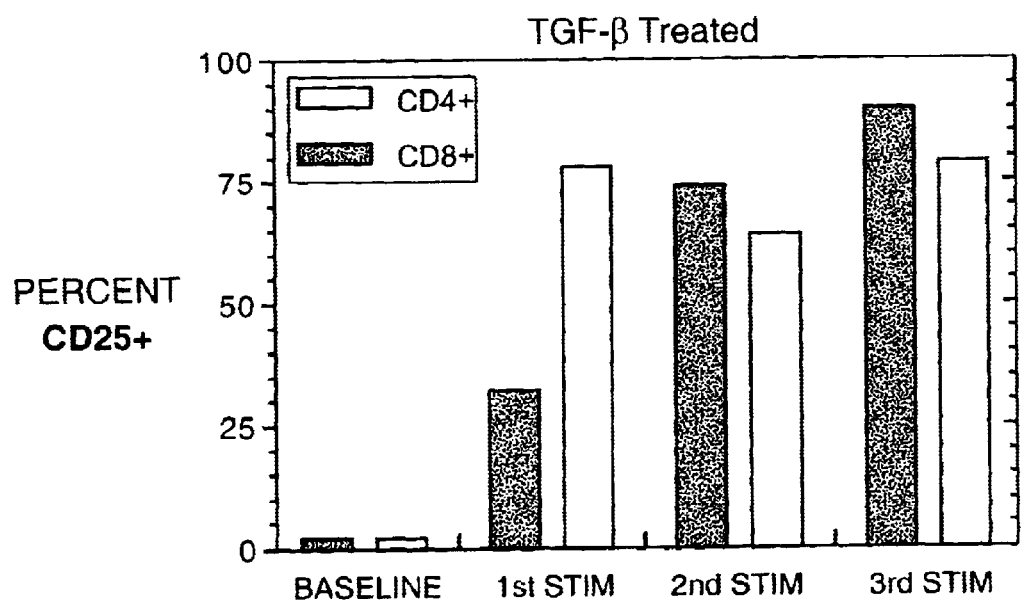
FIG._17D

USE OF CYTOKINES, CELLS AND MITOGENS TO INHIBIT GRAFT VERSUS HOST DISEASE

This application claims the benefit of the filing date U.S. Ser. No. 60/151,987, filed Sep. 1, 1999, and is a continuation of U.S. Ser. No. 09/261,890, filed Mar. 3, 1999, now U.S. Pat. No. 6.447,765, which claims the benefit of the filing date of U.S. Ser. No. 60/076,677, filed Mar. 3, 1998.

FIELD OF THE INVENTION

The field of the invention is generally related to pharmaceutical agents useful in treating graft-versus-host disease (GVHD) in patients that have received allogenic bone marrow transplants.

BACKGROUND OF THE INVENTION

Organ transplantation is now used with great success to improve the quality of human life. Substantial progress has been made in using kidneys, hearts, and livers from unrelated individuals. However, transplantation of hematopoietc stem cells from an unrelated (or allogeneic) donor is a more complicated endeavor. Here multipotent stem cells which have the capacity to regenerate all the blood-forming elements and the immune system are harvested from bone marrow or peripheral blood from one individual are transferred to another. However, histocompatibility differences between donor and recipient results in a higher incidence of transplant-related complications, and has limited the use of this procedure (Forman et al., *Blackwell Scientific Publications*, 1994).

It is unfortunate that only a few individuals are candidates for allogeneic hematopoietc stem cell transplantation at the present time because the spectrum of diseases treatable by this procedure has steadily increased. These diseases now include hematologic malignancies such as the acute or chronic leukemias, multiple myeloma, myelodysplastic syndromes; lymphomas; and the severe anemias such as aplastic anemia or thalassemia.

Allogeneic stem cell transplantation begins with treatment of the recipient with a highly Immunosuppressive conditioning regimen. This is most commonly accomplished with high doses of chemotherapy and radiation which effectively kill ail the blood forming elements of the bone marrow. Besides preparing the recipient bone marrow for donor stem cell transplantation, the conditioning regimen serves to kill much of the malignancy that remains in the body. The period of time between the completion of the conditioning regimen, and engraftment of the donor stem cells is the most dangerous for the recipient. It is during this time that the patient is completely immunocompromised and susceptible to a host of life-threatening infections. This vulnerability persists until the grafted donor stem cells proliferate and differentiate into the needed white blood cells and immune cells needed to combat infections.

Moreover, donor stem cell preparations generally contain immune cells called T lymphocytes. Unless the donor stem cells originate from an identical twin the transferred T cells turn against the recipients tissues and trigger a deadly ailment called graft versus host disease (or GVHD). This is because the donor T lymphocytes recognize histocompatibility antigens of the recipient as foreign and respond by causing multi-organ dysfunction and destruction.

Current techniques of immunosuppression have made allogeneic stem cell transplantation from a related, histocompatible (HLA-matched) donor much safer than it once was. Allogeneic stem cell transplantation from an unrelated, HLA-matched donor is commonly complicated by serious, often fatal GVHD. The threat of GVHD is even higher when the stem cell donor is HLA mismatched.

Since only 30% of patients in need of allogeneic stem cells will have a sibling with identical histocompatibility antigens (Dupont, B., *Immunol Reviews* 157:12, 1997), there is a great need to make HLA-matched unrelated, and HLA-mismatched transplantation a safer procedure. There have been two principal approaches to resolving this problem. The first has been to deplete the graft of contaminating T lymphocytes and the second has been to inactivate the T cells so they cannot attack the recipient.

In the 1970's it became evident that ex-vivo removal of mature T lymphocytes from a bone marrow graft prior to transplantation dramatically decreased or prevented GVHD in animals receiving marrow grafts across major histocompatibility barriers (Rodt, H. J. *Immunol* 4:25–29, 1974; and 4 Vallera et al., *Transplantation* 31:218–222, 1981). However, with T cell depletion the incidence of graft failure, graft rejection, relapse of leukemia, and viral-induced lympho-proliferative disease markedly increased (Martin et al. *Blood* 66:664–672, 1985; 6 Patterson et al. Br J *Hematol* 63:221–230, 1986; Goldman et al. *Ann Intern Med* 108:808–414, 1988; and Lucas et al. *Blood* 87:2594–2603, 1996). Thus, the transplantation of donor T cells on the stem cells has beneficial as well as deleterious effects. One needs the facilitating effect of the T cells on the engraftement of stem cells and the now well recognized graft-versus-tumor effects, but not graft-versus host disease.

Several approaches have been used to decrease T cell activation. These include: 1) in vivo immunosuppressive effects of drugs such as FK506 and rapamycin (Blazar et al. *J. Immunol* 153:1836–1846, 1994; Dupont et al. *J. Immunol* 144:251–258, 1990; Morris *Ann NY Acad Sci* 685:68–72. 1993; and Blazar et al. *J Immunol* 151:5726–5741, 1993); 2) the in vivo targeting of GVHD-reactive T cells using intact and F(ab')2 fragments of monoclonal antibodies(mAb) reactive against T cell determinants or mAb linked to toxins (Gratama et al. *Am j kidney Dis* 11:149–152, 1984; Hiruma et al. *Blood* 79:3050–3058, 1992; Anasetti et al. *Transplantation* 54:844–851, 1992;. Martin et al. *Bone Marrow Transplant* 3:437–444, 1989); 3) inhibition of T cell signaling via either IL-2/cytokine receptor interactions (Herve et al. *Blood* 76:2639–2640, 1990) or the inhibition of T cell activation through blockade of co-stimulatory or adhesogenic signals (Boussiotis et al. *J Exp Med* 178:1753–1763, 1993; Gribben et al. *Blood* 97:4887–4893, 1996; and Blazar et al. *Immunol Rev* 15779–90, 1997); 4) the shifting of the balance between acute GVHD-inducing T helper-type 1 T cells to anti-inflammatory T helper-type 2 T cells via the cytokine milieu in which these cells are generated (Krenger et al. *Transplantation* 58:1251–1257, 1994; Blazar et al. *Blood* 88:247, 1996, abstract; Krenger et al. *J Immunol* 153:585–593. 1995; Fowler et al. *Blood* 84:3540–3549, 1994); 5) the regulation of alloreactive T cell activation by treatment with peptide analogs which affect either T cell receptor/major histocompatibility complex (MHC) interactions, class II MHC/CD4 interactions, or class I MHC/CD8 interactions (Townsend and Kormgold (unpublished data)); and 6) the use of gene therapy to haft the attack of donated cells on the recipients tissues (Bonini et al. *Science* 276:1719–24, 1997).

There is suggestive evidence that the T lymphocytes from non-identical donors can become tolerant to the recipient's tissues. Unlike patients who receive solid organ allografts for whom life-long immunosuppressive therapy is needed to control chronic rejection, there is evidence of immnunologic tolerance with stem cell allografts. The majority of these patients can be withdrawn from immune suppression without further evidence of GVHD (Storb et al. *Blood* 80:560–561, 1992; and Sullivan et al. *Semin Hematol* 28.250–259, 1992).

Immunologic tolerance is a specific state of non-responsiveness to an antigen. Immunologic tolerance generally involves more than the absence of an immune response; this state is an adaptive response of the immune system, one meeting the criteria of antigen specificity and memory that are the hallmarks of any immune response. Tolerance develops more easily in fetal and neonatal animals than in adults, suggesting that immature T and B cells are more susceptible to the induction of tolerance. Moreover, studies have suggested that T cells and B cells differ in their susceptibility to tolerance induction. Induction of tolerance, generally, can be by clonal deletion or clonal anergy. In clonal deletion, immature lymphocytes are eliminated during maturation. In clonal anergy, mature lymphocytes present in the peripheral lymphoid organs become functionally inactivated.

Following antigenic challenge stimulation, T cells generally are stimulated to either promote antibody production or cell-mediated immunity. However, they can also be stimulated to inhibit these immune responses instead. T cells with these down-regulatory properties are called "suppressor cells".

Although it is known that T suppressor cells produce cytokines such as transforming growth factor beta (TGF-beta), interleukin 4 (IL-4) or interleukin (IL-10) with immunosuppressive effects, until recently the mechanisms responsible for the generation of these regulatory cells have been poorly understood. It was generally believed that CD4+ T cells induce CD8– T cells to develop down-regulatory activity and that interleukin 2 (IL-2) produced by CD4+ cells mediates this effect. Although most immunologists agree that IL-2 has an important role in the development of T suppressor cells, whether this cytokine works directly or indirectly is controversial (Via et al. *International Immunol* 5:565572, 1993; Fast, *J Immunol* 149:15101515, 1992; Hirohata et al. *J Immunol* 142:3104–3112, 1989; Taylor, *Advances Exp Med Biol* 319:125–135, 1992; and Kinter et al., *Proc. Natl. Acad. Sci. USA* 92:10985–10989, 1995). Recently, IL-2 has been shown to induce CD8+ cells to suppress HIV replication in CD4– T cells by a non-lytic mechanism. This effect is cytokine mediated, but the specific cytokine with this effect has not been identified (Barker et al. *J Immunol* 156:4476–83, 1996; and Kinter et al. *Proc Natl Acad Sci USA* 99:10985–9 1995).

A model using human peripheral blood lymphocytes to study T cell/B cell interactions in the absence of other accessory cells has been developed (Hirokawa et al. *J. Immunol.* 149:1859–1866, 1992). With this model it was found that CD4+ T cells by themselves generally lacked the capacity to induce CD8+ T cells to become potent suppressor cells. The combination of CD8+ T cells and NK cells, however, induced strong suppressive activity (Gray et al. *J Exp Med* 180:1937–1942, 1994). It was then demonstrated that the contribution of NK cells was to produce TGF-beta in its active form. It was then reported that a small non-immunosuppressive concentration (10–100 pg/ml) of this cytokine served as a co-factor for the generation of strong suppressive effects on IgG and IgM production (Gray et al. *J Exp Med* 180:1937–1942, 1994). Further, it was demonstrated that NK cells are the principal lymphocyte source of TGF-beta (Gray et al. *J Immunol*, 160:2248–2254, 1998).

TGF-beta is a multifunctional family of cytokines important in tissue repair, inflammation and immunoregulation (Border et al. *J Clin Invest* 90:1–7, 1992; and Sporn et al. *J Cell Biol* 105:1039–1045, 1987). TGF-beta is unlike most other cytokines in that the protein released is biologically inactive and unable to bind to specific receptors (Massague, *Cell* 69:1067–1070, 1992). The conversion of latent to active TGF-beta is the critical step which determines the biological effects of this cytokine.

There is some evidence that NK cell-derived TGF-beta has a role in the prevention of GVHD. Whereas the transfer of stem cells from one strain of mice to another histocompatibility mismatched strain resulted in death of all recipients from GVHD within 19 days, the simultaneous transfer of NK cells from the donor animals completely prevented this consequence. All the recipient mice survived indefinitely. This therapeutic effect, however, was completely blocked by antagonizing the effects of TGF-beta by the administration of a neutralizing antibody (Murphy et al. *Immunol Rev* 157:167–176, 1997).

It is very likely, therefore, that the mechanism whereby NK cell-derived TGF-beta prevented GVHD is similar to that described by Horwitz et al., in the down-regulation of antibody production (Horwitz et al., (1998) *Arthritis. Rheum.*, 41:838–844). In each case NK cell-derived TGF-beta was responsible for the generation of suppressor lymphocytes that blocked these respective immune responses. The mouse study is of particular interest since the histocompatibility differences between genetically disparate inbred mice strains would mirror that of unrelated human donors. A modification of this strategy, therefore might overcome GVHD in mismatched humans.

Anti-CD2 monoclonal antibodies and other constructs that bind to the CD2 co-receptor have been shown to be immunosupressive. It has now been demonstrated that at least one mechanism to explain this immunosuppressive effect is by inducing the production of TGF-beta (Gray et al. *J Immunol,* 160:2248–2254, 1998).

One strategy to prevent GVHD would be to isolate and transfer NK cells along with the stem cells. Another would be to treat the immunocompromised recipient who has received allogeneic stem cells with TGF-beta, anti-CD2 monoclonal antibodies, IL-2 or a combination of these cytokines. The first strategy would be difficult because NK cells comprise only 10 to 20% of total lymphocytes so that it would be difficult to harvest a sufficient number of cells for transfer. The second strategy is limited by the systemic toxic side effects of these monoclonal antibodies and cytokines. IL-2 and TGF-beta have numerous effects on different body tissues and are not very safe to deliver to a patient systemically. What is needed, therefore, is a way to induce mammalian cells to suppress the development of GVHD ex vivo.

An approach which generates regulatory T cells ex vivo would provide an effective means of suppressing the development of GVHD. A first step towards achieving the goal of generating regulatory T cells ex vivo is to identify T cells which have potent suppressive effects. There is compelling evidence that in addition to CD8+ cells, certain CD4+ cells have potent suppressive effects. This evidence is based upon the following observations. The first is that injection of peripheral T cells from normal mice depleted of CD45RB™ CD4+ CD25+ T cells into athymic mice results in a high incidence of organ-specific autoimmune disease (Powrie F, et al., *J Exp Med* 183:2669–74, 1996). The second is that certain strains of neonatally thymectomized mice develop multi-organ specific autoimmunity (Powrie F, et al., *J Exp Med* 183:2669–74, 1996; Sakaguchi, S., et al., *J Exp Med* 161(1):72–87, 1985). Taken together, these observations suggest that the normal immune system contains autoreactive T cells capable of inducing severe autoimmune disease, but that this result can be prevented by regulatory T cells. This suggestion has been confirmed by the observation that the autoimmune syndromes described above were prevented by the transfer of C04+ CD25+ T cells (Asano, M., et al., *J Exp Med* 184:387–396, 1996; Sakaguchi, S, et al., *J Immunol* 155:1151–1164, 1995; Read, et al., J. Exp. Med., 192 (2):295–302, 2000). These CD4+ CD25+ differentiate in the thymus and are exported to the periphery where they suppress the activation of potentially self-reactive cells (Asano, M., et al., *J Exp Med* 184:387–396, 1996; Sakaguchi, S, et al., *J Immunol* 155:1151–1164, 1995; Papiemik, M., et al.,*J. Immunol.* 158:4642–4653, 1997; Suri-Payer, E., et al., *J. Immunol.* 160:1212–1218, 1998; Jackson, A. L., et al., *Clin. Immunol. Immunopathol.* 54(1):126–133, 1990; Kanegane, H., et al., *Int. Immunol.* 3(12):1349–1356, 1991). Neonatal mice lack CD4+ CD25+ cells because they are not produced until 1 week after birth (Asano, M., et al., *J Exp Med* 184:387396, 1996; Suri-Payer E, et al., Eur. J. Immunol 29:669–677, 1999).

Thus, CD4+ CD25+ T cells are potent inhibitors of polyclonal T cell activation (Thornton, A. M., and Shevach, E. M.,*J. Exp. Med.* 188:287–296, 1998). After activation via the T cell receptor (TCR), they inhibit IL-2 production by the responding T cells (Takahashi, T., et al., *Int. Immunol.* 10:1969–80, 1998; Thornton, A. M., and Shevach, E. M.,*J. Immunol* 164(1):183–190, 1999). Unlike other regulatory T cells, which produce inhibitory cytokines (Powrie F, et al., *J Exp Med* 183:2669–74, 1996; Weiner, H. L., et al., *Annu. Rev. Immunol.* 12:809–837, 1994), these cells suppress inmune responses by a contact-dependent mechanism, at least in vitro (Thornton, A. M., and Shevach, E. M., *J. Immunol.* 164(1):183–190, 1999). Others have described CD4+ CD25+ cells that regulate anergy in neonatally tolerized mice (Gao, Q., et al., *Transplantation.* 68:1891–1897, 1999).

We have found that regulatory CD4+ CD25+ T cells can be generated in the periphery, as well as the thymus, and that TGF-β directs naive CD4+ cells to develop this property. Therefore, in addition to its well described immunosuppressive effects, TGF-β has positive effects on the growth and development of T cells. TGF-β plays a critical role in the differentiation of both CD8+ T cells and CD4+ T cells to become suppressor cells.

Accordingly, a strategy to generate suppressor T cells ex vivo which are hardy and able to proliferate upon introduction into a recipient is desirable. Such a strategy would involve immunizing CD4+ cells against the white blood cells of an unrelated individual in the presence of TGF-β. CD4+ cells immunized in this manner are activated to become CD25+ and develop suppressive properties similar, if not identical, with the naturally occurring thymus-derived CD4+ CD25+ cells. Following stem cell transplantation, these CD4+ CD25+ suppressor cells would be repeatedly re-stimulated by the donor hematopoietc cells and, thus, have long term inhibitory effects.

SUMMARY OF THE INVENTION

In accordance with the objects outlined above, the present invention provides methods for inducing T cell tolerance in a sample of ex vivo peripheral blood mononuclear cells (PBMCs) comprising adding a suppressive-inducing composition to the cells. The suppressive-inducing composition can be IL-2, IL-10, TGF-β, or a mixture.

In an additional aspect, the present invention provides methods for treating donor cells to ameliorate graft versus host disease in a recipient patient The methods comprise removing peripheral blood mononuclear cells (PBMC) from a donor, and treating the cells with a suppressive-inducing composition for a time sufficient to induce T cell tolerance. The cells are then introduced into a recipient patient. The PBMCs can be enriched for CD8+ cells or CD4+, if desired. The methods may additionally comprising adding the treated cells to donor stem cells prior to introduction into the patient.

In an additional aspect, the present invention provides methods for activating T cells to become suppressor cells. The methods comprise treating T cells with TGF-β. The methods may additionally comprise treating T cells with TFG-β in combination with an activating agent.

In an additional aspect, the invention provides kits for the treatment of donor cells comprising a cell treatment container adapted to receive cells from a donor and at least one dose of a suppressive-inducing composition. The kits may additionally comprise written instructions and reagents. The cell treatment container may comprise a sampling port to enable the removal of a fraction of the cells for analysis, and an exit port adapted to enable at least a portion of the cells to be transported to a recipient patient.

BRIEF DESCRIPTION OF THE DRAWINGS

FIGS. 1A and 1B depict that TGF-β can upregulate expression of CD40 Ligand (CD40L) on T cells. Purified T cells were stimulated with PMA (20 ng/ml) and ionomycin (5 $\mu$M) in the presence or absence of TGF-β. After 6 hours the cells were stained with anti-CD40L antibodies. In the absence of TGF-β, there were 30% positive cells (solid line, panel A). With 100 pg/ml of TGF-β, 66% of the cells were positive (solid line, panel B). The dotted line in both panels is the reactivity of a control antibody.

FIGS. 2A, 2B, 2C and 2D depict that TGF-β increases TNF-β expression by CD8+ cells. Purified CD8+ cells were stimulated for 24 hours with ConA (5 $\mu$g/ml)±TGF-β (10 pg/ml)±IL-2 (10 U). During the last 6 hours, monensin (2 $M) was also present to prevent cytokine release. The cells were first stained with anti-CD69 to distinguish the activated cells. Then the cells were fixed (4% parafomaldhyde), permeabilized (0.1% saponin) and stained with anti-TNF-α antibodies.

FIGS. 3A and 3B depict TGF-β enhances IL-2 expression by T cells. Purified T cells were stimulated in the presence or absence of TGFβ (1 ng/ml). In the absence of TGFβ, 36% of the cells were positive (panel A, solid line) whereas with TGF-β, 53% were positive (panel B, solid line).

FIGS. 4A, 4B, and 4C depict that TGF-β can enhance or inhibit cytotoxic activity. Panel A shows the ability of donor T cells to recognize and kill recipient blood cells. In panel B, purified T cells were cultured with irradiated allogenic stimulator cells in the presence or absence of the indicated cytokines. After 48 hours, the cells were washed and after a further 3 days, assayed for cytotoxic activity against $^{31}$Cr-labelled sitmulator ConA blasts. In panel C, purified CD8+ cells were conditioned with the indicated amounts of TGF-β (10 pg/ml). After 48 hours, the cells were washed. After 5 days of culture, cytotoxic activity was determined.

FIG. 5 depicts the suppression of cytotoxic T cell activity against mismatched human cells by CD8+ T cells conditioned by TGF-β. Purified CD8+ cells from donor A were cultured with irradiated T cell-depleted mononuclear cells from unrelated donor B for 48 hours with our without TGF-β at 10 pg/ml. The cells were then washed and added to T cells from donor A and irradiated non-T cells from donor B and cultured for an additional 5 days. Cytotoxicity by donor A T cells against chromium labeled ConA blasts of donor B was measured by a conventional 4 hour chromium release assay. Various effector to target ratios are shown. Open circles: T cells from donor A and non-Te cells from donor B without added CD8+ cells. Closed squares: control CD8+ T cells added. Closed circles: TGF-β treated CD8+ cells added.

FIG. 6 illustrates that naive CD4+ T cells develop potent suppressive activity when activated in the presence of TGF-β. In a two step co-culture procedure, purified T cell subsets from donor A were stimulated for 5 days with irradiated (3000 cry) allogeneic stimulator cells from donor B±TGF-β (1ng/ml). The secondary cultures consisted of mixing the primed T cell subsets with fresh syngeneic T cells in a 1:4 ratio and culturing these cells with irradiated stimulator cells from donor B for 5 days. CTL activity against ConA blasts from donor B was then determined in a standard four hour chromium release assay at the effector to target cell ratios indicated. FIG. 6A depicts alloactivated CD4+ CD45RA+ cells primed with TGF-β markedly suppressed the generation of CTL activity in comparison with control CD4+ cells. Additional controls not shown were CD4+ cells cultured for 5 days with TGF-β, but without allogeneic MHC stimulation. These cells had no suppressive effects. In FIG. 6B, the experimental protocol was similar except that CD8+ CD45RA+ cells were substituted for CD4+ CD45RA+ cells. Under these conditions, priming CD8+ CD45RA+ cells with alloantigens in the presence of TGF-β did not enhance the development of suppressive activity.

FIGS. 7A and B depicts the effect of CD4 cells primed with TGF-beta on allo-cytotoxic T lymphocyte (CTL) activity. The addition of CD4 CD45RA cells that had been cultured for 5 days without stimulators had no effect on CTL activity (result not shown). Culturing these T cells with stimulator cells resulted in modest to moderate suppressive activity. In all experiments, culture of these T cells with TGF-beta 1 ng/ml markedly suppressed, or abolished allo-CTL activity.

FIGS. 8A and 8B demonstrates that regulatory T cells require cell contact to inhibit CTL activity. CD4reg and control CD4+ cells were generated by activating naive CD4 cells with allogeneic stimulator cells±TGF-βas described above. In secondary cultures, CD4reg or control CD4+ cells were either directly mixed with the responder cells or separated from them by a semipermeable membrane using Transwell™ chambers. The Transwell contained CD4+ cells and stimulator cells. The results shown are one of 3 independent experiments.

FIG. 9 depicts that activation of naive CD4+ T cells in the presence of TGF-β enables them to respond more vigorously to alloantigens, accelerates their conversion to the activated phenotype, and increases their viability. Purified naive CD4+ T cells were cultured for 5 days without stimulator cells [gray shaded area], with irradiated allogeneic stimulator cells [thin dotted line], or with stimulatory cells and TGF-β (1 ng/ml) [thick line], and expression of cell surface or intracellular antigens, were determined by flow cytometry. Cells ($10^5$) were labeled with FITC-conjugated (anti-CD4, anti-CD25), phycoerythrin-conjugated (anti-CD45RA, anti-CTLA-4) or CyChrome-conjugated (anti-CD4) mAbs. CTLA-4 expression was analyzed by intracellular staining. To detect apoptotic cells, annexin-V staining was performed according to the manufacturer's instructions. This experiment is representative of at least 5 studies with each marker.

FIG. 10 that CD4reg display CD25 and require remarkably small numbers for potent on suppressive activity. Naive CD4+ T cells primed with irradiated allogeneic stimulator cells±TGF-β (1ng/ml)and CD4reg were separated into CD25+ and CD25− fractions by cell sorting. FIG. 10A depiects the effect of primed CD4+ cells mixed with fresh T cells at a 1:4 ratio. FIG. 10B depicts the effect of various dilutions of these primed CD4+ T cells added to fresh responder cells on the generation of CTL activity. Results shown were performed at an effector to target cell ratio of 100:1. The results shown are representative of 3 similar experiments.

FIG. 11 shows that CD4+ CD25+ T cells can be expanded and retain their potent suppressive effects. The CD4+ CD25+ fraction of naive CD4+ cells primed in the presence of TGF-β were obtained by cell sorting and cultured in the presence of IL-2 (10 U/ml) for 5 days. The percentages indicated were added to fresh T cells and examined for inhibition of the generation of CTL activity. Irradiated CD4+ CD25+ cells served as controls.

FIG. 12 depicts suppression of lymphocyte proliferation by regulatory CD4+ T cells induced with TGF-β. Naive CD4+ T cells from donor A were mixed with stimulator cells as described above and added to fresh responder and stimulator cells at the indicated ratios. The bars show the uptake of tritiated thymidine±SEM after 7 days of culture. The lightly shaded bar (Nil) indicates the proliferative response of the responder T cells without added CD4+ cells. The darkly shaded bar indicates the effect of control CD4+ cells which had been cultured with stimulator cells without TGF-β. The black bar indicates the effect of CD4+ cells that had been mixed with stimulator cells in the presence of TGF-β (1 ng/ml). The effect of these CD4+ cells on the proliferative response of fresh responder cells added to irradiated stimulator cells after 7 days of culture is shown. The bars indicate the mean uptake of tritiated thymidine.

FIG. 13 depicts the regulatory activity of CD25+ C04 T cells. C04+ cells were stimulated with irradiated allogeneic non-T cells±TGF-β (1 ng/ml) for 5 days. After washing, the CD4+ cells were stained with DII and fresh responder T cells were stained with carboxyfluorescein (CFSE), control or TGF-β primed CD4+ cells were added to the responder T cells and all-stimulator cells in a 1:4 ratio. After 5 days, the cells were harvested and analyzed by flow cytometry. The intensity of CFSE in CD8+ cells was determined by gating on DII negative cells. Note that the addition of TGF-β primed CD4+ cells to responder T cells markedly decreased cell division by CD8+ cells.

FIG. 14 cytotoxic T cell activity depicts that CD4reg block the proliferative response of responder T cells to alloantigens and CD8+ T cells are their principal target. In FIG. 14A, CD4reg or primed control CD4+ cells were mixed with fresh T cells in a 1:4 ratio ($10^5$/well) and cultured in triplicate with irradiated stimulator cells ($10^5$/well) for 5 days. The cultures were pulsed with [3H]TdR for the last 18 hours. In FIG. 14B, the phenotype of the cultured CD8+ cells was determined by flow cytometry gating on CD8+ cells. The gray shaded area indicates cells cultured for 5 days without stimulator cells. The thick line indicates CD8 cells cultured with stimulator cells and CD4reg. The thin dotted line indicates alloactivated CD8 cells cultured with control CD4 cells. The lymphocytes ($10^5$) were labeled with FITC-conjugated (anti-CD69), phycoerythrin-conjugated (anti-CD25, anti-CD95) or CyChrome-conjugated (anti-CD8) mAbs. Annexin-V straining, CFSE levels and DNA content by propidium iodide staining are also shown.

FIGS. 15A and 15B depicts that repeated stimulation of T cells with a low dose of staphylococcal enterotoxin B (SEB)

induces T cells to produce immunosuppressive levels of TGF-β. CD4+ T cells were stimulated with SEB (0.01 ng/ml) and irradiated B cells as superantigen presenting cells with our without TGF-β at the times indicated by the arrows. Active TGF-β was measured 2 or 5 days later.

FIG. 16 depicts that repeated stimulation of CD4+ T cells with a low dose of SEB enables these cells to produce Immunosuppressive levels of TGF-β. CD4+ T cells were stimulated with SEB (0.01ng/ml) and irradiated B cells as superantigen presenting cells with or without TGF-β at the times indicated by the arrows. Active TGF-β was measured 2 or 5 days later.

FIGS. 17A–17D) shows the effects of SEB on naive (CD45RA+ CD45RO-) CD4+ and CD8+ T cells. The cells were stimulated with SEB every 5th day for a total of three stimulations. The percentages of each T cell subset and the cells expressing the CD25 IL-2 receptor activation marker were determined after each stimulation. FIGS. 17A and 17C show that if TGF-β 1 ng/ml was included in the initial stimulation, CD4+ T cells became the predominant subset in the cultures after repeated stimulation. FIGS. 17B and 17D show that CD25 expression by SEB stimulated cells decreases by the third stimulation in control cultures. However, CD25 expression remains high if the T cells have been printed with TGF-β.

DETAILED DESCRIPTION OF THE INVENTION

The present invention allows for the transfer of histoincompatible stem cells to humans with a variety of malignant or hereditary diseases using a method to prevent life-threatening graft-versus-host disease. This is accomplished by treatment of donor cells with a combination of alloantigens and/or cytokines ex vivo. The particular advantage of this procedure is that it avoids the removal of donor T cells which facilitate stem cell engraftment and that have the potential to attack any remaining malignant cells. Once a state of tolerance between donor and host has been achieved, non-conditioned donor T cells can be transferred to maximize the beneficial graft-versus-tumor immune response.

This strategy is unlike almost all other treatment modalities currently in use. These cytokines and mitogens described would have severe toxic side effects if administered in vivo. The ex-vivo protocol described avoids these side effects. The ability to successfully engraft histoincompatible stem cells for treatment of life-threatening diseases would be a milestone in medicine.

In addition, a further advantage of the present invention is that it may avoid or minimize the very toxic immunosuppressive medicines that must be given to the recipient to prevent GVHD. These medicines also block the ability of the donor-derived lymphocytes which repopulate the immune system of the recipient from becoming "educated" to their new host Therefore, it is difficult to stop the immunosuppressive drugs, unless an alternative treatment such as the present invention is used.

The strategy of the present invention is to suppress GVHD by inhibiting the T cell response of donor T cells to the recipient's transplantation antigens, and inducing a tolerant state in the donor cells. This result prevents the donor cells from attacking recipient cells. Surprisingly, the methods outlined herein result in not only the suppression of the treated cells, but additionally induces some CD8+ and CD4+ T cells to prevent other donor T cells from killing recipient cells as well, i.e. they become tolerant. That is, the method outlined herein not only decrease the capacity of the donor's cells to attack the recipients cells, but induces some of the donor's cells to assume a surveillance role and prevent other donor cells from mounting an immune attack against the recipient host The net result is for the donor lymphocytes to be tolerant to the histocompatibility antigens of the recipient, but does not impair the ability of the new lymphocytes to attack tumor cells.

Another significant potential advantage of this strategy is a low probability of serious adverse side effects. Since only trace amounts of suppressive-inducing compositions such as cytokines will be returned to the patient, there should be minimal toxicity.

Accordingly, the present invention is drawn to methods of treating donor cells for transplantation into a recipient that comprise removing peripheral blood mononuclear cells (PBMCs) from the donor and treating the cells with a composition that is on one hand suppressive, but on the other hand generates surveillance cells to prevent an immune attack.

The present invention shows that the treatment of the donor cells with a suppressive-inducing composition blocks an immune attack against the recipients cells. Without being bound by theory, it appears that there are several ways the methods of the invention may work. First of all, the donor cells are activated to become tolerant to the recipient's cells. Secondly, the donor cells are activated to become regulatory cells, that is, as regulatory cells they act to prevent other donor cells from proliferating in response to the recipient's cells and killing them. These results lead to amelioration of a GVHD response. Without being bound by theory, it appears that the inhibition of cytotoxic activity may occur as a result of inhibitory cytokines that are produced by the regulatory T cells such as TGF-β on the cells or a contact-dependent mechanism as depicted in the Figures.

Thus, in a preferred embodiment, the present invention induces tolerance in the donor cells to recipient tissue, thus avoiding GVHD, by treating them with a suppressive-inducing composition ex vivo.

Accordingly, the present invention provides methods of treating donor cells to induce or establish tolerance to recipient cells prior to transplantation into a recipient patient to decrease or eliminate a graft-versus-host response. By "T cell tolerance" herein is meant the failure of T cells to mount a harmful immune response against other cells. This can be due to the failure of T cells to proliferate in response to antigens, or failure to become cytotoxic T cells. Without being bound by theory, this may be due to anergy or death of the T cells. Preferably, the T cells retain the ability to recognize other antigens as foreign, to facilitate tumor killing and general immunological responses to foreign antigens.

Using the methods of the present invention, tolerance is established by treating a population of T cells ex vivo with a suppressive-inducing composition. Regulatory cells are generated by treating a population of T cells ex vivo with an activating agent and a suppressive-inducing composition.

Using the methods outlined herein, a GVHD response is suppressed or treated. By "treating" GVHD herein is meant that at least one symptom of the GVHD is ameliorated by the methods outlined herein. This may be evaluated in a number of ways, including both objective and subjective factors on the part of the patient as is known in the art. For example, GVHD generally exhibits a skin rash, an abnormality in liver function studies, fever, general symptoms including fatigue, anemia, etc.

By "patient" herein is meant a mammalian subject to be treated, with human patients being preferred. In some cases, the methods of the invention find use in experimental animals and in the development of animal models for disease, including, but not limited to, rodents including mice, rats, and hamsters; and primates.

The methods provide for the removal of blood cells from a patient. In general, peripheral blood mononuclear cells (PBMCs) are taken from a patient using standard techniques. By "peripheral blood mononuclear cells" or "PBMCs" herein is meant lymphocytes (including T-cells, B-cells, NK cells, etc.) and monocytes. As outlined more fully below, it appears that the main effect of the suppressive-inducing composition is to enable CD8+ T or CD4+ T cells to become tolerant and to develop the capacity to render other T cells tolerant. Accordingly, the PBMC population should at least comprise CD8+ or CD4+ T cells.

Preferably, only PBMCs are taken, either leaving or returning red blood cells and polymorphonuclear leucocytes to the patient This is done as is known in the art, for example using leukophoresis techniques. In general, a 5 to 7 liter leukophoresis step it done, which essentially removes PBMCs from a patient, returning the remaining blood components. Collection of the cell sample is preferably done in the presence of an anticoagulant such as heparin, as is known in the art.

In some embodiments, as is outlined in Example 7, no leukophoresis step is required. For example, a population of naive CD4+ T cells, when stimulated in the presence of TGF-β, can expand, as shown in FIG. 11.

In general, the sample comprising the PBMCs can be pretreated in a wide variety of ways. Generally, once collected, the cells can be additionally concentrated, if this was not done simultaneously with collection or to further purify and/or concentrate the cells. The cells may be washed, counted, and resuspended in buffer transferred to a sterile, closed system for further purification and activation.

The PBMCs are generally concentrated for treatment, using standard techniques in the art in a preferred embodiment, the leukophoresis collection step results in a concentrated sample of PBMCs, in a sterile leukopak, that may contain reagents or doses of the suppressive composition, as is more fully outlined below. Generally, an additional concentration/purification step is done, such as Ficoil-Hypaque density gradient centrifugation as is known in the art. Separation or concentration procedures include but are not limited to magnetic separation, using antibody-coated magnetic beads, affinity chromatography, cytotoxic agents, either joined to a monoclonal antibody or used with complement, "panning", which uses a monoclonal antibody a to a solid matrix. Antibodies attached to solid matrices, such as magnetic beads, agarose beads, polystyrene beads, follow fiber membranes and plastic surfaces, allow for direct separation. Cells bound by, antibody can be removed or concentration by physically separating the solid support from the cell suspension. The exact conditions a and procedure depend on factors specific to the system employed. The selection of appropriate conditions is well within the skill in the art.

Antibodies may be conjugated to biotin, which then can be removed with avidin or streptavidin bound to a support, or fluorochromes, which can be used with a fluorescence activated cell sorter (FACS), to enable cell separation. Any technique may be employed as long as it is not detrimental to the viability of the desired cells.

In a preferred embodiment, the PBMCs are separated in a automated, closed system such as the Nexell Isolex 300i Magnetic Cell Selection System. Generally, this is done to maintain sterility and to insure standardization of the methodology used for cell separation, activation and development of suppressor cell function.

Once purified or concentrated the cells may be aliquoted and frozen, preferably, in liquid nitrogen or used immediately as described below. Frozen cells may be thawed and used as needed.

Cryoprotective agents, which can be used, include but are not limited to dimethyl sulfoxide (DMSO) (Lovelock, J. E. and Bishop, M. W. H., 1959, *Nature* 183:1394–1395; Ashwood-Smith, M. J., 1961, *Nature* 190:1204–1205), hetastarch, glycerol, polyvinylpyrrolidine (Rinfret, A. P., 1960, Ann. N.Y. Acad. Sci. 85:576), polyethylene glycol (Sloviter, H. A. and Ravdin, R. G., 1962, *Nature* 196:548), albumin, dextran, sucrose, ethylene glycol, i-erythritol, D-ribitol, D-mannitol (Rowe, A. W., et al., 1962, Fed. Proc. 21:157), D-sorbitol, i-inositol, D-lactose, choline chloride (Bender, M. A., et al., 1960, J. Appl. Physiol. 15:520), amino acids (Phan The Tran and Bender, M. A, 1960, *Exp. Cell Res.* 20:851), methanol, acetamide, glycerol monoacetate (Lovelock. J. E., 1954, Biochem. J. 56:265), and inorganic salts (Phan The Tran and Bender, M. A., 1960, Proc. Soc. Exp. Biol. Med. 104:388; Phan The Tran and Bender, M. A., 1961, in Radiobiology Proceedings of the Third Australian Conference on Radiobiology, Ilbery, P. L. T., ed., Butterworth, London, p. 59). Typically, the cells may be stored in 10% DMSO, 50% serum, and 40% RPMI 1640 medium. Methods of cell separation and purification are found in U.S. Pat. No. 5,888,499, which is expressly incorporated by reference.

In a preferred d embodiment, the PBMCs are then washed to remove serum protein s and soluble blood components, such as autoantibodies, inhibitors, etc., using techniques well known in the art Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors of TGF-β) although buffers such as Hanks balanced salt solution (HBBS) or physiological buffered saline (PBS) can also be used.

Generally, the cells are then counted; in general from $1\times10^9$ to $2\times10^9$ white blood cells are collected from a 5–7 liter leukophoresis step. These cells are brought up roughly 200 mls of buffer or media.

In a preferred embodiment, the PBMCs may be enriched for one or more cell types. For example, the PBMCs may be enriched for CD8+ T cells, CD4+ T cells or stem cells. Cell types other than stem cells may be enriched for using commercially available immunoabsorbent columns, or using research procedures (the PBMCs are added to a nylon wool column and the eluted, nonadherent cells are treated with antibodies to CD4, CD16, CD11b, and CD74, followed by treatment with immunomagnetic beads, leaving a population enriched for CD8+ T cells). As more fully described below, isolation of stems cells, e.g., CD34+ stem cells, is done as is known in the art in a closed system using the Nexell separator.

In a preferred embodiment, cell populations are enriched for either CD8+ or CD4+ cells. In other embodiments, other cell types may be enriched for, such as CD3+CD4−CD8− or NK cells.

An advantage of using PBMCs is that other cell types within the PBMC population produce TGF-β, thus decreasing or even eliminating the requirement of the suppressive-inducing composition comprising TGF-β. Thus, in some embodiments, no enrichment step is used.

In a preferred embodiment, the CD4+ cells may be further purified to include only undifferentiated, naive cells. This is done by depleting them of CD45RO+ cells using monoclonal antibodies. This procedure eliminates populations of CD4+ cells which may have acquired functions which might interfere with the generation or activity of suppressor T cells.

Once the cells have undergone any necessary pretreatment, the cells are treated with a suppressive-inducing composition. By "treated" in this context herein is meant that the cells are incubated with the suppressive-inducing composition for a time period sufficient to result in T cell tolerance, particularly when transplanted into the recipient patient. The incubation will generally be under physiological temperature.

A suppressive-inducing composition includes at least one compound which induces T cells to become tolerant to a recipients cells. By "suppressive-inducing composition " herein is meant a composition that can induce T cell tolerance. Generally, these compositions are cytokines. Suitable suppressive-inducing compositions include, but are not limited to, IL-10, II-2, II4, II15 and TGF-β.

Compounds used to induce T cell tolerance include, but are not limited to, prostalandins, nitric oxide, chemokines, cytokines and T cell activators. In a preferred embodiment, the compound used to induce tolerance is a cytokine.

A suppressive-inducing composition containing more than one compound may be used to induce T cells to become tolerant. The suppressive-inducing composition may contain more than one compound from the same class of compounds, i.e., two or more cytokines, chemokines, or prostaglandins may be mixed together. A suppressive-inducing composition also may contain compounds from different classes of compounds, such as a cytokine and a chemokines, or a cytokine and a prostaglandin, etc.

In a preferred embodiment, the suppressive-inducing composition comprises a mixture of cytokines, including TGF-β.

The concentration of the suppressive-inducing composition will vary depending on the identity of the composition, but will generally be at physiologic concentration, i.e. the concentration required to give the desired effect, i.e. an enhancement of specific types of regulatory cells. In a preferred embodiment, TFG-β is used in the suppressive-inducing composition. By "transforming growth factor-β" or "TGF-β" herein is meant any one of the family of the TGF-β, including the three isoforms TGF-β1, TGF-β2, and TGF-β3; see Massague, (1980), *J. Ann. Rev. Cell Biol* 6:597. Lymphocytes and monocytes produce the β1 isoform of this cytokine (Kehrl et al. (1991), *Int J Cell Cloning* 9:438450). The TFG-β can be any form of TFG-β that is active on the mammalian cells being treated.

In humans, recombinant TFG-β is currently preferred. A human TGF-β2 can be purchased from Genzyme Pharmaceuticals, Farmington, Mass. In general, the concentration of TGF-β used ranges from about 2 picograms/ml of cell suspension to about 2 nanograms, with from about 10 pg to about 500 pg being preferred, and from about 50 pg to about 150 pg being especially preferred, and 100 pg being ideal. In general, for immunosuppressive effects, about 1 ng/ml appears optimal. For the generation of suppressor cells it appears lower concentrations (e.g. about 0.1 ng/ml) are optimal.

In some embodiments, IL-2 is used as the suppressive-inducing composition. The IL-2 can be any form of IL-2 that is active on the mammalian cells being treated. In humans, recombinant IL-2 is currently preferred. Recombinant human IL-2 can be purchased from Cetus, Emeryville, Calif. In general, the concentration of IL-2 used ranges from about 1 Unit/ml of cell suspension to about 100 U/ml, with from about 5 U/ml to about 25 U/ml being preferred, and with 10 U/ml being especially preferred. In a preferred embodiment, IL-2 is not used alone.

In a preferred embodiment, the invention provides methods for treating T cells with a suppressive-inducing composition and T cell activators, to generate regulatory T cells. A population of T cells which develop the capacity to prevent other T cells from proliferating and killing the recipients cells, are referred to herein as "regulatory cells" or "suppressor cells".

By "T cell activator" herein is meant a compound which stimulates the expression of cytokine receptors. Suitable T cell activators include anti-CD3 and anti-CD28 antibodies anti-CD2 antibodies combinations of monoclonal antibodies, specific autoantigens if known, cells from a transplant recipient (i.e. alloantigens), IL-2, IL-4, IL-15 and mitogens, such as Concanavalin A or staphylococcus enterotoxin B (SEB).

In a preferred embodiment cells are treated with a suppressive-inducing composition containing cytokine and a T cell activator. For example, cells from a transplant recipient may be used as the T cell activator in combination with a suppressive-inducing composition comprising TGF-β. Similarly, T cell activators such as anti-D3 and anti-CD28 antibodies, anti-CD2 antibodies, Concanavalin A (Con A), or staphylococcus enterotoxin B (SEB) may be used with TGF-β. Other combinations of suppressive-inducing compositions and T cell activators are also possible, such as using the CD2 ligand, LFA-3 and cytokines such as IL-2, IL-4, and TNF-α.

When a mitogen, such as Concanavalin A or staphylococcus enterotoxin B (SEB) is used to stimulate the expression of cytokine receptors, it is generally used as is known in the art, at concentrations ranging from 1 μg/ml to about 10 μg/ml. In addition, it may be desirable to wash the cells with components to remove the mitogen, such as α-methyl mannoside, as is known in the art In a preferred embodiment, CD2 activators, such as a anti CD2 antibodies, which may include the CD2 ligand LFA-3, are used as activating agents. CD2 is a cell surface glycoprotein expressed by T lymphocytes. By "CD2 activator" herein is meant compound that will initiate the CD2 signaling pathway. A preferred CD2 activator comprises anti CD2 antibodies (OKT11, American Type Culture Collection, Rockville Md. and GT2, Huets, et al., (1986) J. Immunol. 137:1420). In general, the concentration of CD2 activator used will be sufficient to induce the production of TGF-β. The concentration of anti CD2 antibodies used ranges from about 1 ng/ml to about 10 μg/ml, with from about 10 ng/ml to about 100 ng/ml being especially preferred.

In a preferred embodiment, cells from the transplant recipient are used to activate the donor CD4+ or CD8+ T cells. TGF-β is used in the suppressive-inducing composition which may also include other cytokines such as IL-2, IL4, and IL-15 to facilitate the effects of TGF-β.

The suppressive-inducing composition is incubated with the donor cells and a population of irradiated PMBC recipient cells (harvested as outlined above). The recipient cells are irradiated so that they cannot attack the donor cells, but will stimulate the donor cells to become tolerant to the recipient cells. The incubation occurs for a period of time sufficient to cause an effect, generally from 4 hours to 5 days although both shorter and longer time periods are possible.

Thus, the recipient cells function as an antigen-specific T cell activator. This activation is necessary for the generation of regulatory cells. Without being bound by theory, it appears that the recipient cells upregulate cytokine receptors on the donor cells, thereby enabling the donor cells to become responsive to TGF-β and develop into regulatory cells.

In a preferred embodiment CD4+ T cells are treated with a suppressive-inducing composition comprising TGF-β and a T cell activator to develop contact-dependent suppression. These regulatory Ace T cells are extremely potent and exert their suppressive effects even when they comprise <1% of the total T cells.

In a preferred embodiment, regulatory CD4+ T cells may be expanded without effecting the suppressive properties of the cells. Preferably, CD4+ T cell may be expanded at least once. More preferably, CD4+ T cells may be expanded up to fourteen fold. More preferably, CD4+ cells may be expanded even further.

In a preferred embodiment, CD4+ T cells activated in the presence of TGF-β and repeatedly stimulated to produce immunosuppressive levels of active TGF-β. By "immunosuppressive levels of active TGF-β" herein is meant a concentration of TGF-β that has a direct immunosuppressive effect on cell function, that is, a concentration of TGF-β that renders the donor cells non responsive to a recipients histocompatibility antigens. In general, concentrations of TGF-β>500 pg/ml have immunosuppressive effects on cell function.

In one embodiment, treatment of the donor cells with the suppressive-inducing composition is followed by immediate transplantation into the recipient patient, generally after the cells have been washed to remove the suppressive-inducing composition. In this embodiment, after the donor cells have been conditioned or treated with the suppressive-inducing composition, they may be frozen or otherwise stored.

In a preferred embodiment, a second step is done comprising obtaining a population of donor hematopoietic stem cells from aspirated bone marrow or PBMCs. Stem cells comprise a very small percentage of the white blood cells in blood, and are isolated as is known in the art, for example as described in U.S. Pat. Nos. 5,635,387 and 4,865,204, both of which are incorporated by reference in their entirety, or harvested using commercial systems such as those sold by Nexell. As outlined above, CD34+ stem cells can be concentrated using affinity columns; the eluted cells are a mixture of CD34+ stem cells and lymphocytes. The contaminating lymphocytes are generally be removed using known techniques such as staining with monoclonal antibodies and removal using conventional negative selection procedures.

Once the CD34+ stem cells have been isolated, they may be mixed with the donor cells previously treated with the suppressive-inducing composition and immediately introduced into the recipient patient.

In one embodiment, the cells are treated for a period of time, washed to remove the suppressive-inducing composition, and may additionally reincubated. The cells are preferably washed as outlined herein to remove the suppressive-inducing composition. Further incubations for testing or evaluation may also be done, ranging in time from a few hours to several days. If evaluation of any cellular characteristics prior to introduction to a patient is desirable, the cells may be incubated for several days to several weeks to expand numbers of suppressor cells.

Once the cells have been treated, they may be evaluated or tested prior to transplantation into the patient For example, a sample may be removed to do: sterility testing; gram staining, microbiological studies; LAL studies; mycoplasma studies; flow cytometry to identify cell types; functional studies, etc. Similarly, these and other lymphocyte studies may be done both before and after treatment. A preferred analysis is a test using labeled recipient cells; incubating the treated tolerant donor cells with a labeled population of the recipient cells will verify that the donor cells are tolerant and won't kill the recipient cells.

In a preferred embodiment, the treatment results in the conditioning of the T cells to become non-responsive to histocompatibility antigens of the recipient so that GVHD is prevented.

In a preferred embodiment, prior to transplantation, the amount of total or active TGF-β can also be tested. As noted herein, TGF-β is made as a latent precursor that is activated post-translationally.

After the cell treatment, the donor cells are transplanted into the recipient patient The MHC class I and class II profiles of both the donor and the recipient are determined. Preferably, a non-related donor is found that preferably matches the recipients HLA antigens, but may mismatch at one or more loci if a matched donor cannot be identified. The recipient patient has generally undergone bone marrow ablation, such as a high dose chemotherapy treatment, with or without total body irradiation.

The donor cells are transplanted into the recipient patient. This is generally done as is known in the art, and usually comprises injecting or introducing the treated cells into the patient as will be appreciated by those in the art. This may be done via intravascular administration, including intravenous or intraarterial administration, intraperitoneal administration, etc. For example, the cells may be placed in a Fenwall infusion bag by injection using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well.

After reintroducing the cells into the patient, the effect of the treatment may be evaluated, if desired, as is generally outlined above and known in the art.

The treatment may be repeated as needed or required. After a period of time, the leukemic cells may reappear. Because the donor lymphocytes are now tolerant to the recipient's cells, the patient now receives a transfusion of unconditioned donor lymphocytes which recognize the leukemic cells as foreign and kill these cells.

In a preferred embodiment, the invention further provides kits for the practice of the methods of the invention, i.e., the incubation of the cells with the suppressive-inducing compositions. The kit may have a number of components. The kit comprises a cell treatment container that is adapted to receive cells from a donor. The container should be sterile. In some embodiments, the cell treatment container is used for collection of the cells, for example it is adaptable to be hooked up to a leukophoresis machine using an inlet port. In other embodiments, a separate cell collection container may be used.

The form and composition of the cell treatment container may vary, as will be appreciated by those in the art. Generally, the container may be in a number of different forms, including a flexible bag, similar to an IV bag, or a rigid container similar to a cell culture vessel. It may be configured to allow stirring. Generally, the composition of the container will be any suitable, biologically inert material, such as glass or plastic, including polypropylene, polyethylene, etc. The cell treatment container may have one or more inlet or outlet ports, for the introduction or removal of cells, reagents, suppressive-inducing compositions, etc. For example, the container may comprise a sampling port for the removal of a fraction of the cells for analysis prior to introduction into the recipient patient. Similarly, the container may comprise an exit port to allow introduction of the cells into the recipient patient; for example, the container may comprise an adapter for attachment to an IV setup.

The kit further comprises at least one dose of a suppressive-inducing composition. "Dose" in this context means an amount of the suppressive-inducing composition such as cytokines, that is sufficient to cause an effect. In some cases, multiple doses may be included. In one embodiment, the dose may be added to the cell treatment container using a port; alternatively, in a preferred embodiment, the dose is already present in the cell treatment container. In a preferred embodiment, the dose is in a lyophilized form for stability, that can be reconstituted using the cell media, or other reagents.

In some embodiments, the kit may additionally comprise at least one reagent, including buffers, salts, media, proteins, drugs, etc. For example, mitogens can be included.

In some embodiments, the kit may additional comprise written instructions for using the kits.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All patents, patent applications, publications and references cited herein are expressly incorporated by reference.

EXAMPLES

Example 1

Treatment of Donor CD8+ Cells Ex Vivo to Suppress an Immune Attack Against Blood Cells of an Unrelated Recipient A blood sample from a donor was obtained and lymphocytes prepared by density gradient centrifugation. T cells were prepared using a conventional negative selection procedure. These T cells were conditioned to prevent them from attacking the recipient cells. For this conditioning, the C08+ T cells were mixed with irradiated stimulator cells from the recipient. The stimulator cells were derived from T cell-depleted blood cells from the recipient. The mixture of donor T cells and recipient stimulator cells were cultured for 48 hours with different concentrations of one or more cytokines. In this example the cytokines were TGF-β and IL-10. This procedure abolished the potential of the donor T cells to kill recipient cells, in FIG. 4B.

To test the ability of the donor T cells to recognize and kill recipient blood cells, the donor T cells were cultured with irradiated stimulator cells for 5 days. Then the donor cells were cultured for 4 hours with a sample of recipient radiolabeled blood cells. When the recipients cells are killed they release radioisotope into the culture medium. By determining the amount of radioisotope released, one can calculate the percentage of cells killed. In the standard cytotoxicity assay shown in FIG. 4A, donor cells were cultured with labeled recipient cells in 30 to 1, 15 to 1, and 7.5 to 1 ratios. These combinations of donor and recipient cells are called effector to target ratios. Killing is indicated by the symbols. As expected, maximum killing was seen at the highest effector to target cell ratio. In FIG. 4A, the open circles shows that if 30 donor cells were mixed with 1 recipient cell, 40 percent of the recipient calls were killed. When donor T cells were conditioned with very small concentrations of TGF-β (0.01 or 0.1 nanograms per ml), they had no effect on killing (FIG. 4D). However, if the T cells were treated with 1 nanogram per ml of TGF-β, the killing of recipient cells decreased by 50 percent. FIG. 4B shows that if the T cells were treated with IL-10, killing also decreased by 50%. If the T calls had been conditioned with both IL-10 and TGF-β at 1 nanogram per ml, these cells completed blocked the killing of recipient cells; killing was almost undetectable. Various combinations of mitogens, cytokines, and monoclonal antibodies can be used to make T cells non-responsive.

Example 2

Treatment of Donor CD8+ T Cells Ex Vivo to Prevent Other Donor T Cells from Mounting an Immune Attack Against Blood Cells from an Unrelated Individual (i.e. Inhibiting GVHD)

CD8+ cells can be conditioned by TGF-β to suppress the cytotoxic immune response of one individual against the cells of an unrelated donor. In this manner, one can assess the cytotoxic activity of donor A against donor B's histocompatibility mismatched blood mononuclear cells. To develop suppressor cells, purified CD8+ cells from donor A were cultured with irradiated T cell-depleted mononuclear cells from donor B with TGF-β added. Separately, the cytotoxic activity of donor A's T cells against donor B cells was documented. FIG. 5 shows that the addition of TGF-β conditioned CD8+ T Cells from donor A significantly decreased the resulting cytotoxic activity. The addition of control CD8+ cells had a minimal effect. In these experiments, CD8+ T cells from donor A were activated by foreign antigens displayed by donor B cells. Additional IL-2 was not needed. These experiments reveal that TGF-β not only induces CD8+ T cells to suppress antibody production, but also induces CD8+ cells to suppress cell-mediated immune responses.

Example 3

Treating a Patient with Chronic Myelocytic Leukemia with the Stem Cells from a Histoincompatible Donor Tolerization with Mitogens The harvested PBMC of the donor are placed in a sterile container in HBBS as in Example 1. The cells are then incubated with mitogens to induce lymphocytes to become non-responsive to histocompatibility antigens of the recipient. In this case the cells are incubated with physiological concentrations of concanavalin A (ConA) for 4 to 72 hours using standard incubation techniques. The concentration of ConA used can range from about 0.01 to about 10 micrograms/ml with 1 microgram/ml being presently preferred. Alternatively, SEB maybe used as the mitogen at concentrations of 0.001 to 100 ng/ml.

The incubation of the mononuclear cells in the mitogen solution increases the population of T suppressor cells. These cells, when transferred to the recipient, will enable the stem cells to engraft without causing GVHD. Although it is not known how the mitogens work, it is believed to induce the production of TGF-beta by certain mononuclear cells in preparation, and the TGF-beta acts on T cells to become suppressor cells ro to directly redner other T cells non responsive.

After the cells have been incubated with the mitogens, the cells are washed with HBBS to remove any nitogens that are in the solution. The cells are suspended in 200–500 ml of HBBS, mixed with the stem cells and administered to a patient with CML who has been treated with myeloablative agents to prepare the stem cells for engraftment.

Once the donor hematopoietic cells lymphocites engraft in the recipient, and the patient again becomes healthy and free of leukemic cells. If the leukemic cells recur, the patient receives a transfusion of donor lymphocites and the leukemic cells again disappear.

Example 4

Treating a Patient with Chronic Myekocytic Leukemia with the Stem Cells from a Histoincompatible Donor: use of Anti-CD2 Monoclonal Antibodies to Induce Production of TGF-β

The harvested enriched stem cell preparation of the donor are placed in a sterile container in HBBS as in Example 1. The cells are then incubated with anti-CD2 monoclonal antibodies to induce lymphocytes to become non-responsive to histocompatibility antigens of the recipient. In this case, the cells are incubated with anti-CD2 monoclonal antibodies for 4 to 72 hours using standard incubation techniques. The concentration of anti-CD2 monoclonal antibodies are 10 ng/ml to 10 ug/ml. Optionally, 1–1000 units of IL-2 can be added.

The incubation of the mononuclear cells in the anti-CD2 solution increases the population of T suppressor cells. These cells, when transferred to the recipient will enable the stem cells to engraft without causing GVHD. It is believed that incubation with anti-CD2 monoclonal antibodies induces the production of TGF-beta by certain monuclear cells in preparation, and the TGF-beta acts on T cells to become suppressor cells.

After the cells have been incubated with the anti-CD2 monoclonal antibodies, the cells are washed with HBBS to remove antibodies that are in the solution. The cells are suspended in 200–500 ml of HBBS mixed with the stem cells harvested previously and administered to a patient with CML who has been treated with myeloblative agents to prepare the stem cells for engraftment.

Once the donor hematopoietic cells lymphocytes engraft in the recipient, and the patient again becomes healthy and free of leukemic cells. If the leukemic cells recur, the patient receives a transfusion of donor lymphocytes and the leukemic cells again disappear.

Example 5

Treating a Patient with Chronic Myelocytic Leukemia with the Stem Cells from a Histoincompatible Donor: Tolerization with Mitogens and Cytokines The harvested PBMC of the donor are placed in a sterile container HBBS as in Example 1. The cells are then incubated with cytokines and mitogens to induce lymphocytes to become non-responsive to histocompatibility antigens of the recipient. In this case the cells are incubated with physiological concentrations of ConA or SEB, TGF-beta, and/or IL-2, IL-4 or IL-15 and for 4 to 72 hours using standard incubation techniques.

After the cells have been incubated with the cytokines and mitogens, the cells are washed with HBBS to remove any cytokine and mitogen that are in the solution. The cells are suspended in 200–500 ml of HBBS mixed with the stem cells and administered to a patient with CML who has been treated with myeloabative agents to prepare the stem cells for engraftment.

Once the donor hematopoietic cells and lymphocytes engraft in recipient and the patient again becomes healthy and free of leukemic cells. If the leukemic cells recur, the patent receives a transfusion of donor lymphocytes and the leukemic cells again disappear.

Example 6

Treating a Patient with Chronic Myalocytic Leukemia with the Stem Cells from a Histoincompatible Donor; Tolerization with a Mitogen and Cytokine The harvested PBMC of the donor are placed in a sterile container in HBBS as in Example 1. The cells are then incubated with a cytokine and a mitogen to induce lymphocytes to become non-responsive to histocompatibility antigens of the recipient in this case the cells are incubated with physiological concentrations of ConA, and IL-2 for 4 to 72 hours using standard incubation techniques. In another case, SEB could be used.

After the cells have been incubated with the cytokines and mitogens, the cells are washed with HBBS to remove any cytokine and mitogen that are in the solution. The cells are suspended in 200–500 ml of HBBS mixed with stem cells and administered to a patient with CML who has been treated with myeloablative agents to prepare the stem cells for engraftment.

Example 7

Effects of TGF-β on Purified CD8+ Cells

Treatment of CD8+ with TGF-β effects CD8+ cells in at least three ways. First, treatment of T cells with PMA (20 ng/ml) and ionomycin (5 $\mu$M) in the presence TGF-β upregulates the expression of CD40 Ligand (FIG. 1). Secondly, IL-2 expression is in enhanced in T cells stimulated with ConA in the presence of TGF-β (FIG. 3). Thirdly, TGF-β increases TNFα expression by CD8+ cells when purified CD8+ cells are stimulated for 24 hours with ConA (5 $\mu$g/ml)±TGF-β (10 /ml)±IL-2 (10 U (FIG. 2).

Example 7

Treatment of CD4+ Cells Ex Vivo to Prevent an Immune Attack

Instead of using mitogens to induce regulatory T cells, the allogeneic mixed lymphocyte reaction is used for this purpose. In this reaction, T cells from donor A recognize and respond to foreign histocompatibility antigens displayed by PBMCs from donor B. These responder T cells proliferate and develop the capacity to kill donor B's cells.

To develop suppressor T cells, various CD4+ cell subsets from donor A were cultured with irradiated T cell-depleted mononuclear cells from donor B. The cells were cultured for 5 days with or without TGF-β (1 ng/ml) in the suspensions.

After this time, TGF-β was removed and the cells added to fresh T cells from donor A and non-T cells from donor B.

Naive CD4+ cells developed potent suppressive activity when activated in the presence of TGF-β. These CD4+ T cells had the capacity to block the generation of CTL activity against allogeneic target cells. In a two step co-culture experiment, CD4+ CD45RA+ RO-T cells were first incubated with irradiated allogeneic stimulator cells±TGF-β for 5 days. Various numbers of these cells were then added to fresh T cells and stimulator cells and the effect of these cells on the generation of CTL activity was assessed. Whereas control CD4+ cells had minimal to moderate suppressive activity, those that had been primed in the presence of TGF-β almost completely blocked responder T cells from killing allogeneic target cells in a standard 4 hour chromium release assay (FIG. 6A). Activation of CD4+ cells was needed for the development of inhibitory activity. T cells cultured with TGF-β without stimulation do not develop this suppressive effect (20). CD4+ suppressor cells primed with alloantigens in the presence of TGF-β are referred to herein as ° CD4reg. Naive CD8+ T cells primed with stimulator cells also develop moderate suppressive activity, but unlike CD4+ cells, the presence of TGF-β did not enhance this activity (FIG. 6B).

FIG. 7 shows two additional experiments with CD4+ regulatory T cells induced by TGF-β.

Further studies revealed that regulatory CD4+ T cells generated in this manner have a unique mode of action. Unlike the CD8+ and CD4+ T cells generated previously which suppress by secreting inhibitory cytokines, these allo-specific regulatory CD4+ T cells have a contact dependent mechanism of action (FIG. 8).

Activation of naive CD4+ T cells in the presence of TGF-β enabled them to respond more vigorously to alloantigens, accelerated their conversion to the activated phenotype, and increased their viability. FIG. 9 indicates properties of control and TGF-β conditioned CD4+ cells after 5 days of culture. Allo-stimulated CD4+ cells displayed the typical features of activation and some were already undergoing activation-induced cell death as indicated by Annexin V staining. Importantly, those alloactivated in the presence of TGF-β were even larger, a fraction stained more intensely with CD4, and expression of CD25 was markedly increased. In 13 experiments mean values for CD25 expression increased from undetectable levels in naive cells to 42.3±3.6% of CD4+ cells alloactivated in the presence of TGF-β. Mean values for control alloactivated CD4+ cells were 34.5±3.8%, (p<0.01%, paired t test). Intracellular and surface expression of CTLA-4 was increased in CD4reg compared with control CD4+ cells (intracellular 31.5±4.1% vs. 23.2±4.5%, p<0.01: surface: 10.8±0.9% vs. 5.2±0.4%, p<0.01). A greater percentage of CD4reg had downregulated surface expression of CD45RA. Significantly, annexin V staining was markedly decreased and the total number of CD4reg recovered was 56% greater than control CD4+ cells. Thus, although CD4reg were more intensively activated that control CD4+ cells, they were also more resistant to activation-induced apoptosis.

Similar to the murine CD4+ regulatory T cells described by Shevach and co-workers (Sun-Payer, E., et al.l, *J. Immunol.* 160:1212–1218, 1998; Suri-Payer, E., et al., *Eur. J. Immunol.* 29:669–677, 1999; Thornton, A. M., and Shevach, E. M., *J. Exp. Med.* 188:287–296, 1998), separation of CD4reg into CD25+ and CD25 fractions by cell sorting revealed that almost all of the suppressive activity was contained in the CD25+ fraction (FIG. 10A). The CD4+ CD25− fraction displayed only minimal suppressive activity. Moreover, the CD4+ CD25+ were very potent as indicated by their ability to markedly inhibit the generation of CTL activity in very low numbers. FIG. 10B shows that suppressive activity was only slightly diminished when the numbers of the CD4+ suppressor cells was reduced from 25 to 3 percent of total T cells: With this small number of added CD4+ cells the minimal suppressive activity mediated by the CD25− subset had disappeared.

Unlike CD4+ regulatory T cells generated by repeated stimulation with IL-10, which have low proliferative capacity (Groux, H., et al., *Nature.* 389:737–742. 24, 1997), CD4reg induced in the presence of TGF-β proliferated in response to IL-2 and retained their suppressive capacity. The CD25+ fraction of CD4reg was isolated by cell sorting and cultured for 5 days with IL-2. These cells expanded 7 to 14 fold during this time and retained their suppressive function in three separate experiments. FIG. 11 shows strong inhibition of the generation of CTL activity when these CD4reg comprised only 5% of the total T cells. Moreover, this suppressive activity remained when the number of these CD4+ CD25 cells was reduced to only 0.2% of total cells. Irradiation of these regulatory T cells, however, abolished their suppressive effects.

Addition of these T cells to responder T cells and allostimulator cells inhibited proliferation (FIG. 12) and decreased the ability of responder CD8+ killer precursor cells to become activated (FIG. 13).

CD4reg blocked the proliferative response of responder T cells to alloantigens (FIG. 14B) and CD8+ T cells were the principal target Gating on CD8+ cells by flow cytometry after a 5 day culture, alloactivated CD8+ cells displayed the expected marked increase in CD25, increased expression of CD69 and Fas, and evidence of cell division by CFSE-labeled and propidium iodide-labeled effector T cells. Moreover, some CD8+ cells were undergoing activation-induced cell death as indicated by annexin V staining. In sharp contrast, in cultures containing CD4reg, upregulation of CD25, CD69 and Fas by CD8+ cells was markedly inhibited and almost none underwent apoptosis or cell division. Studies of the absolute numbers of CD8+ cells in culture revealed only a minimal change from the total count. Thus, CD4reg rendered CD8+ cells anergic.

Example 9

CD4+ T Cells can be Stimulated to Produce Immunosuppressive Levels of TGF-β

CD4+ T cells that produce immunosuppressive levels of TGF-β have been named Th3 cells, but the mechanisms involved in their development are poorly understood. We have obtained evidence that strong stimulation of CD4+ cells with the superantigen, staphylococcus enterotoxin, B (SEB), or repeated stimulation of CD4+ cells stimulated with a lower concentration of SEB induced these cells to produce immunosuppressive levels of active TGF-β.

FIG. 15 shows increased production of both active and total TGF-β produced by CD4+ T cells stimulated with increasing concentrations of SEB. FIG. 16 shows the effect of repeated stimulation of CD4+ T cells with low doses of SEB. By the third time these T cells were stimulated with SEB, they produced significant amounts of the active form of TGF-β.

FIG. 17 shows the effects of SEB on naive (CD45RA+ CD45RO-) CD4+ and CD8+ T cells. The cells were stimulated with SEB every 5 th day for a total of three stimulations. The percentages of each T cell subset and the cells expressing the CD25 IL-2 receptor activation marker were determined after each stimulation. Panels A and C show that by including TGF-β1 ng/ml in the initial stimulation, CD4+ T cells became the predominant subset in the cultures after repealed stimulation. Panels B and D show that CD25 expression by SEB stimulated cells decreased by the third stimulation in control cultures. However, CD25 expression remained very high if the T cells were primed with TGF-β. Thus, TGF-β appears to have preferential effects on CD4+ cells if these T cells are repeatedly stimulated and almost all of these cells were CD25+ after culture for 20 days.

In summary, following T cell stimulation, the initial regulatory effects of TGF-β are directed to CD8+ cells. Upon more prolonged or repeated stimulation, this cytokine now induces CD4+ cells to become regulatory cells and these cells are more potent than CD8+ cells in their suppressive activities.

Example 10

Treating a Patient with Chronic Myelocytic Leukemia who has Developed GVHD Following the Stem Cell Transplant In the instance that the initial procedure to prevent early or late GVHD following the stem cell transplant is not successful, this event will be managed by transfer of a larger number of donor T cells that have been conditioned to become suppressor cells. Approximately $1 \times 10^9$ PBMCs obtained by leukopheresis are concentrated in a sterile leukopak; in Hanks balanced salt solution (HBBS). The PMMCs will be separated into CD4+ and CD8+ cells by magnetic beads coated with the appropriate monoclonal antibodies. The cells will be treated with the desired T cell activating agent and suppressive-inducing composition for the optimum time to develop maximal regulatory activity. The cells will be expanded and then transferred to the recipient. These conditioned T cells migrate to lymphoid organs and suppress the GVHD.

Besides chronic myelcytic leukemia, other hematologic malignancies such as acute and chronic leukemias, lymphomas, solid tumors such as breast carcinoma or renal cell carcinoma among a few, and non-malignant diseases such as severe anemias (thalassemia, sickle cell anemia) can be treated with mismatched allogeneic stem cells.

Another aspect of this invention is a kit to perform the cell incubation with the cytokines. The kit comprises a sterile incubating container with the appropriate concentration of cytokines preloaded within the container. In one embodiment of the kit, the cytokines are present in lyophilized form in the container. The container is preferably a bag, similar to an IV bag. The lyophilized cytokines are reconstituted with HBBS and then the cells are injected into the container and thoroughly mixed and incubated. In another embodiment of the invention the cytokines are already in solution within the container and all that has to be done is the injection of washed stern cell preparation and incubation.

What is claimed is:

1. A method for treating donor cells to ameliorate graft versus host disease in a recipient patient comprising:
    a) removing peripheral blood mononuclear cells (PBMC) from a donor;
    b) treating said PBMC with a suppressive-inducing composition comprising TGF-β, IL-2, and at least one other T cell activator for a time sufficient to induce T cell tolerance in said; treated PMBC and
    c) introducing said treated PBMC to said patient.
2. A method according to claim 1, wherein said other T cell activator is an irradiated recipient PMBC.
3. A method according to claim 1 wherein said method further comprises adding said treated PBMC to donor stem cells prior to introduction into said patient.
4. A method according to claim 1 wherein said PBMC are enriched for CD8+ cells.
5. A method according to claim 1 wherein said PBMC are enriched for CD4+ cells.
6. A method for treating donor cells to ameliorate graft versus host disease in a recipient patient comprising:
    a) removing peripheral blood mononuclear cells (PBMC) from a donor;
    b) treating said PBMC with a suppressive-inducing composition comprising TGF-β, IL-2, and at least one other T cell activator for a time sufficient to generate suppressor cells; and
    c) introducing said suppressor cells to said patient.
7. A method according to claim 6, wherein said other T cell activator is an irradiated recipient PBMC.
8. A method according to claim 6 wherein said method further comprises adding said cells to donor stem cells prior to introduction into said patient.
9. A method according to claim 6, wherein said PMBC are enriched for CD8+ cells.
10. A method according to claim 6, wherein said PMBC are enriched for CD4+ cells.
11. A method for treating donor cells to ameliorate graft versus host disease in a recipient patient comprising:
    a) removing peripheral blood mononuclear cells (PBMC) from a donor;
    b) selectively enriching said PBMC for CD3+CD4−CD8− cells;
    c) treating said CD3+CD4−CD8− cells with a suppressive-inducing composition comprising TGF-β, IL-2 and at least one other T cell activator for a time sufficient to induce T cell tolerance in said treated CD3+CD4−CD8− cells; and
    c) introducing said treated CD3+CD4−CD8− cells to said patient.
12. A method for treating donor cells to ameliorate graft versus host disease in a recipient patient comprising:
    a) removing peripheral blood mononuclear cells (PBMC) from a donor;
    b) selectively enriching said PBMC for CD3+CD4−CD8− cells;
    c) treating said CD3+CD4CD8− cells with a suppressive-inducing composition comprising TGF-β, IL-2 and at least one other T cell activator for a time sufficient to generate suppressor cells; and
    c) introducing said suppressor cells to said patient.
13. A method according to claim 1, 6, 11 or 12 wherein said other T cell activator is an anti-CD3antibody.
14. A method according to claim 1, 6, 11 or 12 wherein said other T cell activator is an anti-CD28 antibody.
15. A method according to claim 1, 6, 11 or 12 wherein said other T cell activator is an anti-CD2 antibody.
16. A method according to claim 1, 6, 11 or 12 wherein said other T cell activator is staphylococcus enterotoxin B.

17. A method for treating donor cells to ameliorate graft versus host disease in a recipient patient comprising:
 a) removing peripheral blood mononuclear cells (PBMC) from a donor;
 b) selectively enriching said PBMC for CD3+CD4−CD8− cells;
 c) treating said CD3+CD4−CD8− cells with a suppressive-inducing composition comprising TGF-β, IL-2 and the T cell activator anti-CD3 anti-CD3 for a time sufficient to induce T cell tolerance in said treated CD3+CD4−CD8− cells, and
 c) introducing said treated CD3+CD4−CD8− cells to said patient.

18. A method for treating donor cells to ameliorate graft versus host disease in a recipient patient comprising:
 a) removing peripheral blood mononuclear cells (PBMC) from a donor;
 b) selectively enriching said PBMC for CD3+CD4−CD8− cells;
 c) treating said CD3+CD4−CD8− cells with a suppressive-inducing composition comprising TGF-β, IL2 and the T cell activator anti-CD3 anti-CD3 for a time sufficient to generate suppressor cells; and
 c) introducing said suppressor cells to said patient.

* * * * *